United States Patent
Berger et al.

(10) Patent No.: US 7,754,759 B2
(45) Date of Patent: Jul. 13, 2010

(54) ARYLSULFONYL CHROMANS AS 5-HT$_6$ INHIBITORS

(75) Inventors: Jacob Berger, Los Altos Hills, CA (US); Joan Marie Caroon, Mountain View, CA (US); Francisco Javier Lopez-Tapia, Union City, CA (US); Lee Edwin Lowrie, Jr., San Jose, CA (US); Dov Nitzan, San Jose, CA (US); Shu-Hai Zhao, Cupertino, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 848 days.

(21) Appl. No.: 11/592,685

(22) Filed: Nov. 3, 2006

(65) Prior Publication Data

US 2007/0099908 A1 May 3, 2007

Related U.S. Application Data

(60) Provisional application No. 60/732,940, filed on Nov. 3, 2005.

(51) Int. Cl.
*A61K 31/353* (2006.01)
*C07D 311/22* (2006.01)
*C07D 311/58* (2006.01)

(52) U.S. Cl. ........................ 514/456; 549/401; 549/405; 549/407

(58) Field of Classification Search .............. 549/401, 549/407; 514/456
See application file for complete search history.

(56) References Cited

U.S. PATENT DOCUMENTS

| | | | |
|---|---|---|---|
| 5,137,901 A | 8/1992 | Junge et al. |
| 5,374,643 A | 12/1994 | Atwal et al. |
| 5,412,117 A | 5/1995 | Koga et al. |
| 5,614,633 A | 3/1997 | Koga et al. |
| 5,627,138 A | 5/1997 | Anderson et al. |
| 5,637,624 A | 6/1997 | Schaus et al. |
| 5,646,308 A | 7/1997 | Koga et al. |
| 5,663,194 A | 9/1997 | Mewshaw |
| 5,719,182 A | 2/1998 | Cousins et al. |
| 5,739,135 A | 4/1998 | Biller et al. |
| 5,869,478 A | 2/1999 | Ding et al. |
| 5,874,446 A | 2/1999 | Koga et al. |
| 5,883,099 A | 3/1999 | Biller et al. |
| 5,935,958 A | 8/1999 | Kozlowski et al. |
| 5,977,167 A | 11/1999 | Koga et al. |
| 6,083,982 A | 7/2000 | Wechter et al. |
| 6,150,402 A | 11/2000 | Wechter et al. |
| 6,214,881 B1 | 4/2001 | Xiang |
| 6,448,243 B1 | 9/2002 | Kitazawa et al. |
| 6,479,536 B1 | 11/2002 | Ohkawa et al. |
| 6,559,144 B2 | 5/2003 | Diefenbach et al. |
| 6,586,475 B1 | 7/2003 | Kato et al. |
| 6,605,632 B1 | 8/2003 | Lesieur et al. |
| 6,613,805 B2 | 9/2003 | Kato et al. |
| 6,638,972 B2 | 10/2003 | Kelly et al. |
| 6,660,752 B2 | 12/2003 | O'Connor et al. |
| 6,706,757 B2 | 3/2004 | Greenblatt et al. |
| 6,784,314 B2 | 8/2004 | Yamashita et al. |
| 7,378,415 B2 | 5/2008 | Sethofer et al. |
| 2002/0002177 A1 | 1/2002 | Cousins et al. |
| 2003/0060498 A1 | 3/2003 | Fu |
| 2003/0153599 A1 | 8/2003 | Kelly et al. |
| 2003/0158175 A1 | 8/2003 | Greenblatt et al. |
| 2004/0024210 A1 | 2/2004 | Johansson et al. |
| 2004/0077867 A1 | 4/2004 | Kato et al. |
| 2004/0087577 A1 | 5/2004 | Pratt et al. |
| 2004/0097492 A1 | 5/2004 | Pratt et al. |
| 2004/0162285 A1 | 8/2004 | Pratt et al. |
| 2004/0167123 A1 | 8/2004 | Pratt et al. |
| 2005/0075331 A1 | 4/2005 | Pratt et al. |
| 2005/0154053 A1 | 7/2005 | Rhijn et al. |
| 2005/0215594 A1 | 9/2005 | O'Connor et al. |
| 2006/0167255 A1 | 7/2006 | Greenhouse et al. |

FOREIGN PATENT DOCUMENTS

| | | |
|---|---|---|
| EP | 0 488 616 A1 | 11/1991 |
| EP | 0 496 238 A1 | 1/1992 |
| EP | 0 587 180 A2 | 9/1993 |
| EP | 0 747 374 B1 | 12/2001 |
| WO | 9520587 A1 | 8/1995 |
| WO | WO 96/05191 | 2/1996 |

(Continued)

OTHER PUBLICATIONS

Dhanak, D., et al. "Identification and Biological Characterization of Heterocyclic Inhibitors of the Hepatitis C Virus RNA-dependent RNA Polymerase," *J. Biological Chem.* vol. 277. No. 41 (2002) pp. 38322-38327.

Gu, B. et al. "Arresting Initiation of Hepatitis C Virus RNA Synthesis Using Heterocyclic Derivatives," *J. Biological Chem.* vol. 278, No. 19 (2003) pp. 16602-16607.

Nguyen, T.T., et al., "Resistance Profile of a Hepatitis C Virus RNA-Dependent RNA Polymerase Benzothiadiazine Inhibitor," *Antimicrobial Agents and Chemotherapy*, vol. 47, No. 11 (2003) pp. 3525-3530.

*Primary Examiner*—Bernard Dentz
(74) *Attorney, Agent, or Firm*—Robert C. Hall

(57) ABSTRACT

Compounds of the formula I:

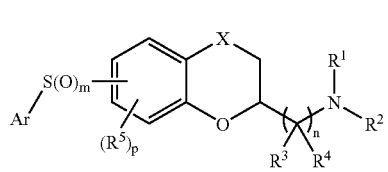

wherein m, n, p, X, Ar, $R^1$, $R^2$, $R^3$, $R^4$ and $R^5$ are as defined herein. Methods of making the compounds and using the compounds for treatment of 5-HT6 receptor-mediated diseases are disclosed.

27 Claims, No Drawings

FOREIGN PATENT DOCUMENTS

| | | |
|---|---|---|
| WO | WO 97/02259 | 1/1997 |
| WO | WO 98/00412 | 1/1998 |
| WO | WO 98/07418 | 2/1998 |
| WO | 9935144 A1 | 7/1999 |
| WO | WO 01/85172 A1 | 11/2001 |
| WO | WO 02/20507 A1 | 3/2002 |
| WO | WO 02/48134 A2 | 6/2002 |
| WO | WO 02/085891 A1 | 10/2002 |
| WO | WO 02/098424 A1 | 12/2002 |
| WO | WO 03/029238 A1 | 4/2003 |
| WO | WO 03/037262 A2 | 5/2003 |
| WO | WO 03/005356 A2 | 7/2003 |
| WO | WO 03/099801 A1 | 12/2003 |
| WO | WO 2004/000828 A1 | 12/2003 |
| WO | WO 2004/052312 A2 | 6/2004 |
| WO | WO 2004/052313 A2 | 6/2004 |
| WO | WO 2004/058150 A2 | 7/2004 |
| WO | WO 2005/019191 A2 | 3/2005 |
| WO | WO 2005/019191 A3 | 3/2005 |
| WO | WO 2005/037223 A2 | 4/2005 |
| WO | WO 2005/040355 A2 | 5/2005 |
| WO | 2005105776 A1 | 11/2005 |

ARYLSULFONYL CHROMANS AS 5-HT$_6$ INHIBITORS

CROSS REFERENCE TO RELATED APPLICATIONS

This application claims the benefit of priority of U.S. Provisional Patent Application Ser. No. 60/732,940 filed Nov. 3, 2005, the disclosure of which is incorporated herein by reference in its entirety.

FIELD OF THE INVENTION

This invention relates to substituted chroman compounds, and associated compositions, methods for use as therapeutic agents, and methods of preparation thereof.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., J. Pharmacol. Exp. Ther., 1994, 268, pages 1403-14120, D. R. Sibley et al., Mol. Pharmacol., 1993, 43, 320-327, A. J. Sleight et al., Neurotransmission, 1995, 11, 1-5, and A. J. Sleight et al., Serotonin ID Research Alert, 1997, 2(3), 115-8.

While some 5-HT6 and 5-HT2A modulators have been disclosed, there continues to be a need for compounds that are useful for modulating the 5-HT6 receptor, the 5-HT2A receptor, or both.

SUMMARY

The invention provides compounds of the formula I:

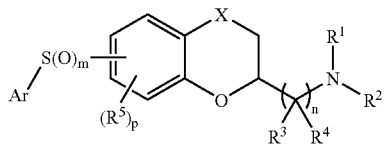

or a pharmaceutically acceptable salt thereof,
wherein:
m is from 0 to 2;
n is from 1 to 3;
p is from 0 to 3;

Ar is optionally substituted aryl or optionally substituted heteroaryl;
X is —C(O)— or —CR$^a$R$^b$—,
wherein:
R$^a$ is hydrogen or C$_{1-6}$alkyl; and
R$^b$ is hydrogen, C$_{1-6}$alkyl or hydroxy;
R$^1$ and R$^2$ each independently is:
hydrogen;
C$_{1-6}$alkyl;
C$_{1-6}$alkoxy-C$_{1-6}$alkyl;
hydroxy-C$_{1-6}$alkyl; or
—CH$_2$—C(O)—OCH$_3$;
or one of R$^1$ and R$^2$ is hydrogen or C$_{1-6}$alkyl and the other is:
  a five- or six-membered heteroaryl or heterocyclyl that contains one or two nitrogens and which is optionally substituted with hydroxyl;
  C$_{3-8}$ cycloalkyl;
  aryl-C$_{1-6}$alkyl; or
  —(CH$_2$)$_r$—Y—R$^h$,
  wherein:
  Y is —C(O)— or —SO$_2$—;
  r is 0, 1 or 2; and
  R$^h$ is:
    C$_{1-6}$alkyl;
    C$_{3-8}$ cycloalkyl;
    C$_{1-6}$alkoxy;
    cyano-C$_{1-6}$alkyl;
    halo-C$_{1-6}$alkyl;
    hydroxy;
    amino;
    N—C$_{1-6}$alkylamino;
    N,N-di-C$_{1-6}$alkylamino;
    hydroxy-C$_{1-6}$alkyl wherein the hydroxy group may be acetylated;
    aryl;
    aryl-C$_{1-6}$alkyl; or
    aryl-C$_{1-6}$alkyloxy-C$_{1-6}$alkyl;
or R$^1$ and R$^2$ together with the nitrogen to which they are attached may form a three- to seven-membered ring that optionally contains an additional heteroatom selected from N, O and S and which is optionally substituted with hydroxyl;
or R$^1$ and R$^2$ together with the nitrogen to which they are attached may form a guanidinyl group or an amidinyl group;
R$^3$ and R$^4$ each independently is hydrogen or C$_{1-6}$ alkyl;
or one of R$^3$ and R$^4$ together with one of R$^1$ and R$^2$ and the atoms to which they are attached may form a five or six-membered ring;
or R$^3$ and R$^4$ together may form =NR$^c$ wherein R$^c$ is hydrogen or C$_{1-6}$ alkyl; and
each R$^5$ is independently halo, C$_{1-6}$ alkyl, halo-C$_{1-6}$ alkyl, hetero-C$_{1-6}$ alkyl, cyano, —SO$_2$R$^d$, —C(=O)—NR$^e$R$^f$, —SR$^d$, —C(=O)—R$^g$, where each of R$^d$, R$^e$ and R$^f$ is independently hydrogen or C$_{1-6}$ alkyl and R$^g$ is hydrogen, C$_{1-6}$ alkyl, hydroxy or C$_{1-6}$ alkoxy.

The invention further provides compositions comprising, methods for making and and methods for using the subject compounds.

DETAILED DESCRIPTION OF THE INVENTION

The invention provides aryl chroman compounds, associated compositions, methods for use as therapeutic agents, and methods of preparation thereof.

All patents and publications cited in this disclosure are incorporated herein by reference in their entirety.

DEFINITIONS

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group or moiety of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkenylene" means a linear unsaturated divalent hydrocarbon radical of two to six carbon atoms or a branched saturated divalent hydrocarbon radical of three to six carbon atoms, e.g., ethenylene (—CH═CH—), 2,2-dimethylethenylene, propenylene, 2-methylpropenylene, butenylene, pentenylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula —R'—R", where R' is alkylene and R" is alkoxy as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —R'—R", where R' is oxo and R" is alkyl as defined herein.

"Alkylsulfonyl" means a moiety of the formula —R'—R", where R' is —$SO_2$— and R" is alkyl as defined herein.

"Alkylsulfonylalkyl" means a moiety of the formula $R^a$—$SO_2$—$R^b$—, where $R^a$ is alkyl and $R^b$ is alkylene as defined herein. Exemplary alkylsulfonylalkyl groups include, by way of example, 3-methanesulfonylpropyl, 2-methanesulfonylethyl, 2-methanesulfonylpropy, and the like.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Amidinyl" means a group of the formula:

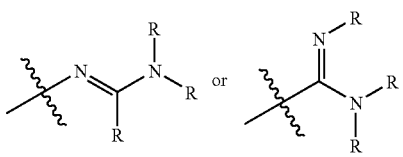

wherein each R independently is hydrogen or alkyl as defined herein.

"Amidinylalkyl" means a group —R—R' wherein R' is amidinyl as defined herein and R is alkylene.

"Amido" means a group —C(O)—NRR' wherein R and R' each independently is hydrogen or alkyl.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Aryloxy" means a moiety of the formula —OR, wherein R is an aryl moiety as defined herein.

"Arylalkyl" and "Aralkyl", which may be used interchangeably, mean a radical-$R^a R^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Aralkoxy" means a moiety of the formula —OR, wherein R is an aralkyl moiety as defined herein.

"Carbamyl means a group of the formula:

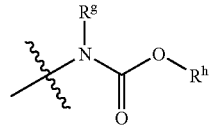

wherein $R^g$ and $R^h$ each independently is hydrogen or alkyl.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Guanidinyl" as used herein means a group of the formula:

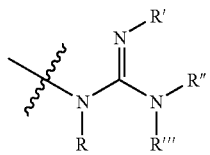

wherein R, R', R" and R'" each independently is hydrogen or alkyl.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroaryloxy" means a moiety of the formula —OR, wherein R is a heteroaryl moiety as defined herein.

"Heteroarylalkyl" and "Heteroaralkyl", which may be used interchangeably, mean a radical-$R^aR^b$ where $R^a$ is an alkylene group and $R^b$ is a heteroaryl group as defined herein.

"Heteroaralkoxy" means a moiety of the formula —OR, wherein R is a heteroaralkyl moiety as defined herein.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. Examples of alkoxy moieties include, but are not limited to, methoxy, ethoxy, isopropoxy, and the like.

"Hydroxyalkyl" refers to a subset of heteroalkyl and refers in particular to an alkyl moiety as defined herein that is substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a group —R—R' wherein R' is heterocyclyl as defined herein and R is alkylene.

"Imidazolinyl" as used herein means a group of the formula:

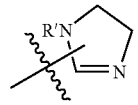

wherein R' is hydrogen or alkyl. Imidazolinyl groups may be optionally substituted as defined herein.

"Imidazolinylalkyl" means a group —R—R' wherein R' is imidazolinyl as defined herein and R is alkylene.

"Imidazolinylaminoalkyl" means a group —R—R'—R" wherein R" is imidazolinyl as defined herein, R' is amino, and R is alkylene. The amino moiety of "imidazolinylaminoalkyl" may be optionally substituted with alkyl.

"Pyrimidinylaminoalkyl" means a group —R—R'—R" wherein R" is pyrimidinyl (preferably pyrimidin-2-yl), R' is amino, and R is alkylene. The pyrimidinyl moiety of "pyrimidinylaminoalkyl" may be optionally substituted as defined herein, and the amino moiety of "pyrimidinylaminoalkyl" may be optionally substituted with alkyl.

"Tetrahydropyrimidinyl" means 1,4,5,6-tetrahydropyrimidinyl, preferably 1,4,5,6-tetrahydropyrimidin-2-yl, and may be optionally substituted as defined herein. "Tetrahydropyrimidinyl" includes 5,5-dimethyl-1,4,5,6-tetrahydropyrimidin-2-yl.

"Tetrahydropyrimidinylaminoalkyl" means a group —R—R'—R" wherein R" is tetrahydropyrimidinyl, R' is amino, and R is alkylene. The amino moiety of "tetrahydropyrimidinylaminoalkyl" may be optionally substituted with alkyl.

"Urea" means a group of the formula:

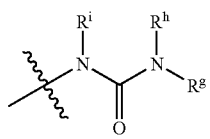

wherein $R^g$, $R^h$ and $R^i$ each independently is hydrogen or alkyl.

"Urealkyl" means a group R—R' wherein R' is urea and R is alkylene.

"Optionally substituted", when used in association with "aryl", phenyl", "heteroaryl" or "heterocyclyl", means an aryl, phenyl, heteroaryl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include: acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Persons skilled in the art will know how to choose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. Numbering of ring positions of the benzodioxane, benzoxazine and benzothiazine compounds of the invention is done according to the formula:

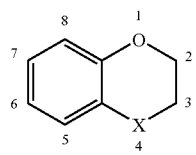

Compounds

The invention provides compounds of the formula I:

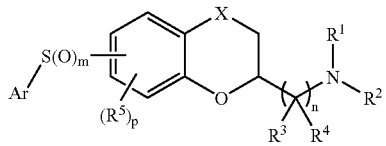

or a pharmaceutically acceptable salt thereof, wherein:

m is from 0 to 2:

n is from 1 to 3;

p is from 0 to 3;

Ar is optionally substituted aryl or optionally substituted heteroaryl;

X is —C(O)— or —$CR^aR^b$—, wherein:

$R^a$ is hydrogen or $C_{1-6}$alkyl; and $R^b$ is hydrogen, $C_{1-6}$alkyl or hydroxy;

$R^1$ and $R^2$ each independently is:

hydrogen;

$C_{1-6}$alkyl;

$C_{1-6}$alkoxy-$C_{1-6}$alkyl;

hydroxy-$C_{1-6}$alkyl; or

—$CH_2$—C(O)—$OCH_3$;

or one of $R^1$ and $R^2$ is hydrogen or $C_{1-6}$ alkyl and the other is:

a five- or six-membered heteroaryl or heterocyclyl that contains one or two nitrogens and which is optionally substituted with hydroxyl;

$C_{3-8}$ cycloalkyl;

aryl-$C_{1-6}$alkyl; or

—$(CH_2)_r$—Y—$R^h$, wherein:

Y is —C(O)— or —$SO_2$—;

r is 0, 1 or 2; and $R^h$ is:

$C_{1-6}$alkyl;

$C_{3-8}$ cycloalkyl;

$C_{1-6}$alkoxy;

cyano-$C_{1-6}$alkyl;

halo-$C_{1-6}$alkyl;

hydroxy;

amino;

N—$C_{1-6}$alkylamino;

N,N-di-$C_{1-6}$alkylamino;

hydroxy-$C_{1-6}$alkyl wherein the hydroxy group may be acetylated;

aryl;

aryl-$C_{1-6}$alkyl; or aryl-$C_{1-6}$alkyloxy-$C_{1-6}$alkyl;

or $R^1$ and $R^2$ together with the nitrogen to which they are attached may form a three- to seven-membered ring that optionally contains an additional heteroatom selected from N, O and S and which is optionally substituted with hydroxyl;

or $R^1$ and $R^2$ together with the nitrogen to which they are attached may form a guanidinyl group or an amidinyl group;

$R^3$ and $R^4$ each independently is hydrogen or $C_{1-6}$ alkyl;

or one of $R^3$ and $R^4$ together with one of $R^1$ and $R^2$ and the atoms to which they are attached may form a five or six-membered ring;

or $R^3$ and $R^4$ together may form =$NR^c$ wherein $R^c$ is hydrogen or $C_{1-6}$ alkyl; and each $R^5$ is independently halo, $C_{1-6}$ alkyl, halo-$C_{1-6}$ alkyl, hetero-$C_{1-6}$ alkyl, cyano, —$SO_2R^d$, —C(=O)—$NR^eR^f$, —$SR^d$, —C(=O)—$R^g$, where each of $R^d$, $R^e$ and $R^f$ is independently hydrogen or $C_{1-6}$ alkyl and $R^g$ is hydrogen, $C_{1-6}$ alkyl, hydroxy or $C_{1-6}$ alkoxy.

It is to be understood that the scope of this invention encompasses not only the various isomers which may exist but also the various mixture of isomers which may be formed. Furthermore, the scope of the invention also encompasses solvates, salts and prodrugs of the subject compounds.

In certain embodiments of formula I, n is 1.

In certain embodiments of formula I, $R^3$ and $R^4$ are hydrogen.

In certain embodiments of formula I, $R^1$ and $R^2$ each independently is hydrogen or $C_{1-6}$alkyl.

In certain embodiments of formula I, Ar is optionally substituted phenyl.

In certain embodiments of formula I, p is 0 or 1.
In certain embodiments of formula I, p is 0.
In certain embodiments of formula I, X is —$CR^aR^b$—.
In certain embodiments of formula I, $R^a$ and $R^b$ are hydrogen.
In certain embodiments of formula I, X is —C(O)—.
In certain embodiments of formula I, n is 2.
In certain embodiments of formula I, m is 0 or 2.
In certain embodiments of formula I, m is 2.
In certain embodiments of formula I, Ar is optionally substituted heteroaryl.
In certain embodiments of formula I, Ar is heteroaryl selected from thienyl, furanyl, pyridinyl and pyrimidinyl, each optionally substituted.
In certain embodiments of formula I, $R^1$ and $R^2$ together with the nitrogen to which they are attached form a three, four, five or six-membered heterocyclic ring that is optionally substituted with hydroxyl.
In certain embodiments of formula I, $R^3$ and $R^4$ together form =$NR^c$ wherein $R^c$ is hydrogen or $C_{1-6}$alkyl.
In certain embodiments of formula I, one of $R^1$ and $R^2$ is hydrogen or $C_{1-6}$ alkyl and the other is $C_{1-6}$alkylcarbonyl, $C_{3-8}$ cycloalkyl, aryl-$C_{1-6}$ alkyl, hydroxy, or a five- or six-membered heteroaryl or heterocyclyl that contains one or two nitrogens.
In certain embodiments of formula I, one of $R^3$ and $R^4$ together with one of $R^1$ and $R^2$ and the atoms to which they are attached form a five or six-membered heterocyclic ring.
In certain embodiments of formula I, $R^1$ and $R^2$ together with the nitrogen to which they are attached form a guanidinyl group, an amidinyl group, a carbamyl group, or a urea group.
In certain embodiments of formula I, $R^1$ and $R^2$ together with the nitrogen to which they are attached form a guanidinyl group or an amidinyl group.
In certain embodiments of formula I, $R^1$ and $R^2$ together with the nitrogen to which they are attached form a three- to seven-membered heterocyclic ring that is optionally substituted with hydroxyl.
In certain embodiments of formula I, $R^1$ and $R^2$ together with the nitrogen to which they are attached form a three- to seven-membered heterocyclic ring that includes an additional heteroatom selected from N, O and S.
In certain embodiments of formula I, $R^1$ and $R^2$ together with the nitrogen to which they are attached form a three-membered heterocyclic ring.
In certain embodiments of formula I, $R^1$ and $R^2$ together with the nitrogen to which they are attached form a four-membered heterocyclic ring that is optionally substituted with hydroxyl.
In certain embodiments of formula I, $R^1$ and $R^2$ together with the nitrogen to which they are attached form a five-membered heterocyclic ring that is optionally substituted with hydroxyl.
In certain embodiments of formula I, $R^1$ and $R^2$ together with the nitrogen to which they are attached form a six-membered heterocyclic ring that is optionally substituted with hydroxyl.
In certain embodiments of formula I, $R^1$ is hydrogen or $C_{1-6}$ alkyl and $R^2$ —$(CH_2)_r$—Y—$R^h$.
In certain embodiments of formula I, $R^1$ is hydrogen or $C_{1-6}$ alkyl and $R^2$ —$CH_2$—C(O)—$R^h$.
In certain embodiments of formula I, $R^1$ is hydrogen or $C_{1-6}$ alkyl and $R^2$ —C(O)—$R^h$.
In certain embodiments of formula I, $R^1$ is hydrogen or $C_{1-6}$ alkyl and $R^2$ —$CH_2$—$SO_2$—$R^h$.
In certain embodiments of formula I, $R^1$ is hydrogen or $C_{1-6}$ alkyl and $R^2$ —$SO_2$—$R^h$.

In certain embodiments of formula I, n is 1 and $R^3$ and $R^4$ are hydrogen.
In certain embodiments of formula I, n is 1, $R^3$ and $R^4$ are hydrogen, and $R^1$ and $R^2$ each independently is hydrogen or $C_{1-6}$alkyl.
In certain embodiments of formula I, n is 1, $R^3$ and $R^4$ are hydrogen, $R^1$ and $R^2$ each independently is hydrogen or $C_{1-6}$alkyl, and X is —$CR^aR^b$—.
In certain embodiments of formula I, n is 1, $R^3$ and $R^4$ are hydrogen, $R^1$ and $R^2$ each independently is hydrogen or $C_{1-6}$alkyl, X is —$CR^aR^b$—, and $R^a$ and $R^b$ are hydrogen.
In certain embodiments of formula I, n is 1, $R^3$ and $R^4$ are hydrogen, $R^1$ and $R^2$ each independently is hydrogen or $C_{1-6}$alkyl, X is —$CR^aR^b$—, $R^a$ and $R^b$ are hydrogen, and p is 0 or 1.
In certain embodiments of formula I, n is 1, $R^3$ and $R^4$ are hydrogen, $R^1$ and $R^2$ each independently is hydrogen or $C_{1-6}$alkyl, X is —$CR^aR^b$—, $R^a$ and $R^b$ are hydrogen, p is 0 or 1, and m is 2.
In certain embodiments of formula I, n is 1, $R^3$ and $R^4$ are hydrogen, $R^1$ and $R^2$ each independently is hydrogen or $C_{1-6}$alkyl, X is —$CR^aR^b$—, $R^a$ and $R^b$ are hydrogen, p is 0 or 1, m is 2, and Ar is optionally substituted phenyl.
In certain embodiments of formula I, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, and $R^a$ and $R^b$ are hydrogen.
In certain embodiments of formula I, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, and Y is —C(O)—.
In certain embodiments of formula I, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, Y is —C(O)—, and r is 1.
In certain embodiments of formula I, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, Y is —C(O)—, r is 1, $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino, and Ar is optionally substituted phenyl.
In certain embodiments of formula I, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, Y is —C(O)—, and r is 0.
In certain embodiments of formula I, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, Y is —C(O)—, r is 0, $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino, and Ar is optionally substituted phenyl.
In certain embodiments of formula I, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, and Y is —$SO_2$—.
In certain embodiments of formula I, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, Y is —$SO_2$—, and r is 1.
In certain embodiments of formula I, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, Y is —$SO_2$—, r is 1, $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino, and Ar is optionally substituted phenyl.

In certain embodiments of formula I, n is 1, $R^3$ and $R^4$ are hydrogen, $R^1$ is hydrogen or $C_{1-6}$alkyl, $R^2$ is —(CH$_2$)$_r$—Y—$R^h$, X is —CR$^a$R$^b$—, R$^a$ and R$^b$ are hydrogen, Y is —SO$_2$—, and r is 0.

In certain embodiments of formula I, n is 1, $R^3$ and $R^4$ are hydrogen, $R^1$ is hydrogen or $C_{1-6}$alkyl, $R^2$ is —(CH$_2$)$_r$—Y—$R^h$, X is —CR$^a$R$^b$—, R$^a$ and R$^b$ are hydrogen, Y is —SO$_2$—, r is 0, $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino, and Ar is optionally substituted phenyl.

In certain embodiments of the invention, the compounds are of formula II:

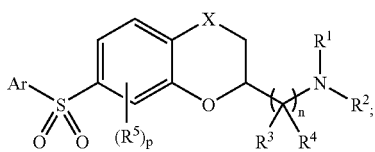

II wherein n, p, X, Ar, $R^1$, $R^2$, $R^3$, $R^4$ and $R^5$ are as defined herein.

In certain embodiments of formula II, n is 1.

In certain embodiments of formula II, $R^3$ and $R^4$ are hydrogen.

In certain embodiments of formula II, $R^1$ and $R^2$ each independently is hydrogen or $C_{1-6}$alkyl.

In certain embodiments of formula II, Ar is optionally substituted phenyl.

In certain embodiments of formula II, p is 0 or 1.

In certain embodiments of formula II, p is 0.

In certain embodiments of formula II, X is —CR$^a$R$^b$—.

In certain embodiments of formula II, R$^a$ and R$^b$ are hydrogen.

In certain embodiments of formula II, X is —C(O)—.

In certain embodiments of formula II, n is 2.

In certain embodiments of formula II, Ar is optionally substituted heteroaryl.

In certain embodiments of formula II, Ar is heteroaryl selected from thienyl, furanyl, pyridinyl and pyrimidinyl, each optionally substituted.

In certain embodiments of formula II, $R^1$ and $R^2$ together with the nitrogen to which they are attached form a three, four, five or six-membered heterocyclic ring that is optionally substituted with hydroxyl.

In certain embodiments of formula II, $R^3$ and $R^4$ together form =NR$^c$ wherein R$^c$ is hydrogen or $C_{1-6}$alkyl.

In certain embodiments of formula II, one of $R^1$ and $R^2$ is hydrogen or $C_{1-6}$ alkyl and the other is $C_{1-6}$alkylcarbonyl, $C_{3-8}$ cycloalkyl, aryl-$C_{1-6}$ alkyl, hydroxy, or a five- or six-membered heteroaryl or heterocyclyl that contains one or two nitrogens.

In certain embodiments of formula II, one of $R^3$ and $R^4$ together with one of $R^1$ and $R^2$ and the atoms to which they are attached form a five or six-membered heterocyclic ring.

In certain embodiments of formula II, $R^1$ and $R^2$ together with the nitrogen to which they are attached form a guanidinyl group, an amidinyl group, a carbamyl group, or a urea group.

In certain embodiments of formula II, $R^1$ and $R^2$ together with the nitrogen to which they are attached form a guanidinyl group or an amidinyl group.

In certain embodiments of formula II, $R^1$ and $R^2$ together with the nitrogen to which they are attached form a three- to seven-membered heterocyclic ring that is optionally substituted with hydroxyl.

In certain embodiments of formula II, $R^1$ and $R^2$ together with the nitrogen to which they are attached form a three- to seven-membered heterocyclic ring that includes an additional heteroatom selected from N, O and S.

In certain embodiments of formula II, $R^1$ and $R^2$ together with the nitrogen to which they are attached form a three-membered heterocyclic ring.

In certain embodiments of formula II, $R^1$ and $R^2$ together with the nitrogen to which they are attached form a four-membered heterocyclic ring.

In certain embodiments of formula II, $R^1$ and $R^2$ together with the nitrogen to which they are attached form a five-membered heterocyclic ring that is optionally substituted with hydroxyl.

In certain embodiments of formula II, $R^1$ and $R^2$ together with the nitrogen to which they are attached form a six-membered heterocyclic ring that is optionally substituted with hydroxyl.

In certain embodiments of formula II, n is 1 and $R^3$ and $R^4$ are hydrogen.

In certain embodiments of formula II, n is 1, $R^3$ and $R^4$ are hydrogen, and $R^1$ and $R^2$ each independently is hydrogen or $C_{1-6}$alkyl.

In certain embodiments of formula II, $R^1$ is hydrogen or $C_{1-6}$ alkyl and $R^2$ is —(CH$_2$)$_r$—Y—$R^h$.

In certain embodiments of formula II, $R^1$ is hydrogen or $C_{1-6}$ alkyl and $R^2$ is —CH$_2$—C(O)—$R^h$.

In certain embodiments of formula II, $R^1$ is hydrogen or $C_{1-6}$ alkyl and $R^2$ is —C(O)—$R^h$.

In certain embodiments of formula II, $R^1$ is hydrogen or $C_{1-6}$ alkyl and $R^2$ is —CH$_2$—SO$_2$—$R^h$.

In certain embodiments of formula II, $R^1$ is hydrogen or $C_{1-6}$alkyl and $R^2$ is —SO$_2$—$R^h$.

In certain embodiments of formula II, n is 1, $R^3$ and $R^4$ are hydrogen, $R^1$ and $R^2$ each independently is hydrogen or $C_{1-6}$alkyl, and X is —CR$^a$R$^b$—.

In certain embodiments of formula II, n is 1, $R^3$ and $R^4$ are hydrogen, $R^1$ and $R^2$ each independently is hydrogen or $C_{1-6}$alkyl, X is —CR$^a$R$^b$—, and R$^a$ and R$^b$ are hydrogen.

In certain embodiments of formula II, n is 1, $R^3$ and $R^4$ are hydrogen, $R^1$ and $R^2$ each independently is hydrogen or $C_{1-6}$alkyl, X is —CR$^a$R$^b$—, R$^a$ and R$^b$ are hydrogen, and p is 0 or 1.

In certain embodiments of formula II, n is 1, $R^3$ and $R^4$ are hydrogen, $R^1$ and $R^2$ each independently is hydrogen or $C_{1-6}$alkyl, X is —CR$^a$R$^b$—, R$^a$ and R$^b$ are hydrogen, p is 0 or 1, and Ar is optionally substituted phenyl.

In certain embodiments of formula II, n is 1, $R^3$ and $R^4$ are hydrogen, $R^1$ is hydrogen or $C_{1-6}$alkyl, $R^2$ is —(CH$_2$)$_r$—Y—$R^h$, X is —CR$^a$R$^b$—, and R$^a$ and R$^b$ are hydrogen.

In certain embodiments of formula II, n is 1, $R^3$ and $R^4$ are hydrogen, $R^1$ is hydrogen or $C_{1-6}$alkyl, $R^2$ is —(CH$_2$)$_r$—Y—$R^h$, X is —CR$^a$R$^b$—, R$^a$ and R$^b$ are hydrogen, and Y is —C(O)—.

In certain embodiments of formula II, n is 1, $R^3$ and $R^4$ are hydrogen, $R^1$ is hydrogen or $C_{1-6}$alkyl, $R^2$ is —(CH$_2$)$_r$—Y—$R^h$, X is —CR$^a$R$^b$—, R$^a$ and R$^b$ are hydrogen, Y is —C(O)—, and r is 1.

In certain embodiments of formula II, n is 1, $R^3$ and $R^4$ are hydrogen, $R^1$ is hydrogen or $C_{1-6}$alkyl, $R^2$ is —(CH$_2$)$_r$—Y—$R^h$, X is —CR$^a$R$^b$—, R$^a$ and R$^b$ are hydrogen, Y is —C(O)—, r is 1, $R^h$ is $C_{1-6}$alkyl, $C_{3-8}$ cycloalkyl, $C_{1-6}$alkoxy, halo-$C_{1-6}$ alkyl, amino, N—$C_{1-6}$alkylamino or N,N-di-$C_{1-6}$alkylamino, and Ar is optionally substituted phenyl.

In certain embodiments of formula II, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, Y is —C(O)—, and r is 0.

In certain embodiments of formula II, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, Y is —C(O)—, r is 0, $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino, and Ar is optionally substituted phenyl.

In certain embodiments of formula II, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, and Y is —$SO_2$—.

In certain embodiments of formula II, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, Y is —$SO_2$—, and r is 1.

In certain embodiments of formula II, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, Y is —$SO_2$—, r is 1, $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino, and Ar is optionally substituted phenyl.

In certain embodiments of formula II, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, Y is —$SO_2$—, and r is 0.

In certain embodiments of formula II, n is 1, $R^3$ and $R^4$ are hydrogen, $R^1$ is hydrogen or $C_{1-6}$alkyl, $R^2$ is —$(CH_2)_r$—Y—$R^h$, X is —$CR^aR^b$—, $R^a$ and $R^b$ are hydrogen, Y is —$SO_2$—, r is 0, $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino, and Ar is optionally substituted phenyl.

In certain embodiments of the invention, the compounds are of formula III:

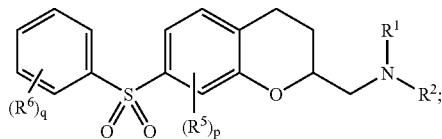

III wherein:
q is from 0 to 4;
each $R^6$ is independently halo, $C_{1-6}$ alkyl, halo-$C_{1-6}$ alkyl, hetero-$C_{1-6}$ alkyl, cyano, —$SO_2R^d$, —C(=O)—$NR^eR^f$, —$SR^d$, —C(=O)—$R^g$, where each of $R^d$, $R^e$ and $R^f$ is independently hydrogen or $C_{1-6}$ alkyl and $R^g$ is hydrogen, $C_{1-6}$ alkyl, hydroxy or $C_{1-6}$ alkoxy; and
p, $R^1$, $R^2$, $R^5$ and $R^6$ are as defined herein.

In certain embodiments of formula III, $R^1$ and $R^2$ each independently is hydrogen or $C_{1-6}$alkyl.

In certain embodiments of formula III, p is 0 or 1.

In certain embodiments of formula III, p is 0.

In certain embodiments of formula III, $R^1$ and $R^2$ together with the nitrogen to which they are attached form a three, four, five or six-membered heterocyclic ring.

In certain embodiments of formula III, one of $R^1$ and $R^2$ is hydrogen or $C_{1-6}$ alkyl and the other is $C_{1-6}$alkylcarbonyl, $C_{3-8}$ cycloalkyl, aryl-$C_{1-6}$ alkyl, hydroxy, or a five- or six-membered heteroaryl or heterocyclyl that contains one or two nitrogens.

In certain embodiments of formula III, $R^1$ and $R^2$ together with the nitrogen to which they are attached form a guanidinyl group, an amidinyl group, a carbamyl group, or a urea group.

In certain embodiments of formula III, $R^1$ and $R^2$ together with the nitrogen to which they are attached form a three- to seven-membered heterocyclic ring that is optionally substituted with hydroxyl.

In certain embodiments of formula III, $R^1$ and $R^2$ together with the nitrogen to which they are attached form a three- to seven-membered heterocyclic ring that includes an additional heteroatom selected from N, O and S.

In certain embodiments of formula III, $R^1$ and $R^2$ together with the nitrogen to which they are attached form a three-membered heterocyclic ring.

In certain embodiments of formula III, $R^1$ and $R^2$ together with the nitrogen to which they are attached form a four-membered heterocyclic ring.

In certain embodiments of formula III, $R^1$ and $R^2$ together with the nitrogen to which they are attached form a five-membered heterocyclic ring that is optionally substituted with hydroxyl.

In certain embodiments of formula III, $R^1$ and $R^2$ together with the nitrogen to which they are attached form a six-membered heterocyclic ring that is optionally substituted with hydroxyl.

In certain embodiments of formula III, q is 0 or 1 and $R^7$ is halo.

In certain embodiments of formula III, $R^1$ is hydrogen and $R^2$ is methyl.

In certain embodiments of formula III, p is 0 or 1, q is 0 or 1, $R^5$ and $R^6$ are halo, $R^1$ is hydrogen and $R^2$ is methyl.

In certain embodiments of formula III, $R^1$ and $R^2$ together with the nitrogen to which they are attached form a guanidinyl group or an amidinyl group.

In certain embodiments of formula III, $R^1$ is hydrogen or $C_{1-6}$ alkyl and $R^2$ is —$(CH_2)_r$—Y—$R^h$.

In certain embodiments of formula III, $R^1$ is hydrogen or $C_{1-6}$ alkyl and $R^2$ is —$CH_2$—C(O)—$R^h$.

In certain embodiments of formula III, $R^1$ is hydrogen or $C_{1-6}$ alkyl and $R^2$ is —C(O)—$R^h$.

In certain embodiments of formula III, $R^1$ is hydrogen or $C_{1-6}$ alkyl and $R^2$ is —$CH_2$—$SO_2$—$R^h$.

In certain embodiments of formula III, $R^1$ is hydrogen or $C_{1-6}$ alkyl and $R^2$ is —$SO_2$—$R^h$.

In certain embodiments of formula III, $R^1$ and $R^2$ each independently is hydrogen or $C_{1-6}$alkyl, and p is 0 or 1.

In certain embodiments of formula III, $R^1$ and $R^2$ each independently is hydrogen or $C_{1-6}$alkyl, p is 0 or 1, and $R^6$ is halo.

In certain embodiments of formula III, $R^1$ is hydrogen or $C_{1-6}$alkyl, and $R^2$ is —$(CH_2)_r$—Y—$R^h$.

In certain embodiments of formula III, $R^1$ is hydrogen or $C_{1-6}$alkyl, $R^2$ is —$(CH_2)_r$—Y—$R^h$, and Y is —C(O)—.

In certain embodiments of formula III, $R^1$ is hydrogen or $C_{1-6}$alkyl, $R^2$ is —$(CH_2)_r$—Y—$R^h$, Y is —C(O)—, and r is 1.

In certain embodiments of formula III, $R^1$ is hydrogen or $C_{1-6}$alkyl, $R^2$ is —$(CH_2)_r$—Y—$R^h$, Y is —C(O)—, r is 1, and $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino.

In certain embodiments of formula III, $R^1$ is hydrogen or $C_{1-6}$alkyl, $R^2$ is —$(CH_2)_r$—Y—$R^h$, Y is —C(O)—, r is 1, $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino, p is 0 or 1, q is 0 or 1, and $R^5$ and $R^6$ are halo.

In certain embodiments of formula III, $R^1$ is hydrogen or $C_{1-6}$alkyl, $R^2$ is —$(CH_2)_r$—Y—$R^h$, Y is —C(O)—, and r is 0.

In certain embodiments of formula III, n is 1, $R^1$ is hydrogen or $C_{1-6}$alkyl, $R^2$ is —$(CH_2)_r$—Y—$R^h$, Y is —C(O)—, r is 0, and $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino.

In certain embodiments of formula III, $R^1$ is hydrogen or $C_{1-6}$alkyl, $R^2$ is —$(CH_2)_r$—Y—$R^h$, Y is —C(O)—, r is 0, $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino, p is 0 or 1, q is 0 or 1, and $R^5$ and $R^6$ are halo.

In certain embodiments of formula III, $R^1$ is hydrogen or $C_{1-6}$alkyl, $R^2$ is —$(CH_2)_r$—Y—$R^h$, and Y is —$SO_2$—.

In certain embodiments of formula III, $R^1$ is hydrogen or $C_{1-6}$alkyl, $R^2$ is —$(CH_2)_r$—Y—$R^h$, Y is —$SO_2$—, and r is 1.

In certain embodiments of formula III, $R^1$ is hydrogen or $C_{1-6}$alkyl, $R^2$ is —$(CH_2)_r$—Y—$R^h$, Y is —$SO_2$—, r is 1, and $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino.

In certain embodiments of formula III, $R^1$ is hydrogen or $C_{1-6}$alkyl, $R^2$ is —$(CH_2)_r$—Y—$R^h$, Y is —$SO_2$—, r is 1, $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino, p is 0 or 1, q is 0 or 1, and $R^5$ and $R^6$ are halo.

In certain embodiments of formula III, $R^1$ is hydrogen or $C_{1-6}$alkyl, $R^2$ is —$(CH_2)_r$—Y—$R^h$, Y is —$SO_2$—, and r is 0.

In certain embodiments of formula III, $R^1$ is hydrogen or $C_{1-6}$alkyl, $R^2$ is —$(CH_2)_r$—Y—$R^h$, Y is —$SO_2$—, r is 0, and $R^h$ is $C_{1-6}$alkyl, $C_{3-8}$cycloalkyl, $C_{1-6}$alkoxy, halo-$C_{1-6}$alkyl, amino, N—$C_{1-6}$alkylamino or N,N-di-$C_{1-6}$alkylamino.

In certain embodiments of formula III, $R^1$ is hydrogen or $C_{1-6}$alkyl, $R^2$ is —$(CH_2)_r$—Y—$R^h$, Y is —$SO_2$—, r is 0, $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino, p is 0 or 1, q is 0 or 1, and $R^5$ and $R^6$ are halo.

In certain embodiments of the invention, the compounds are of formula IV:

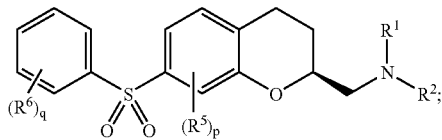

wherein p, q, $R^1$, $R^2$, $R^5$ and $R^6$ are as defined herein.

In certain embodiments of formula IV, $R^1$ and $R^2$ each independently is hydrogen or $C_{1-6}$alkyl.

In certain embodiments of formula IV, p is 0 or 1.

In certain embodiments of formula IV, p is 0.

In certain embodiments of formula IV, q is 0 or 1 and $R^6$ is halo.

In certain embodiments of formula IV, $R^1$ is hydrogen and $R^2$ is methyl.

In certain embodiments of formula IV, p is 0, q is 0 or 1, $R^6$ is halo, $R^1$ is hydrogen and $R^2$ is methyl.

In certain embodiments of the invention, the compounds are of formula V:

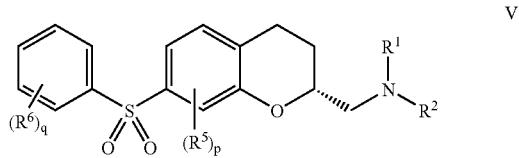

wherein p, q, $R^1$, $R^2$, $R^5$ and $R^6$ are as defined herein.

In certain embodiments of formula V, p is 0 or 1.

In certain embodiments of formula V, p is 0.

In certain embodiments of formula V, q is 0 or 1 and $R^6$ is halo.

In certain embodiments of formula V, $R^1$ is hydrogen and $R^2$ is methyl.

In certain embodiments of formula V, p is 0, q is 0 or 1, $R^5$ and $R^6$ are halo, $R^1$ is hydrogen and $R^2$ is methyl.

In certain embodiments of formula IV or formula V, $R^1$ and $R^2$ together with the nitrogen to which they are attached form a guanidinyl group or an amidinyl group.

In certain embodiments of formula IV or formula V, $R^1$ is hydrogen or $C_{1-6}$ alkyl and $R^2$—$(CH_2)_r$—Y—$R^h$.

In certain embodiments of formula IV or formula V, $R^1$ is hydrogen or $C_{1-6}$ alkyl and $R^2$ —$CH_2$—C(O)—$R^h$.

In certain embodiments of formula IV or formula V, $R^1$ is hydrogen or $C_{1-6}$ alkyl and $R^2$ —C(O)—$R^h$.

In certain embodiments of formula IV or formula V, $R^1$ is hydrogen or $C_{1-6}$ alkyl and $R^2$ —$CH_2$—$SO_2$—$R^h$.

In certain embodiments of formula IV or formula V, $R^1$ is hydrogen or $C_{1-6}$ alkyl and $R^2$ —$SO_2$—$R^h$.

In certain embodiments of formula IV or formula V, $R^1$ and $R^2$ each independently is hydrogen or $C_{1-6}$alkyl, and p is 0 or 1.

In certain embodiments of formula IV or formula V, $R^1$ and $R^2$ each independently is hydrogen or $C_{1-6}$alkyl, p is 0 or 1, and $R^6$ is halo.

In certain embodiments of formula IV or formula V, $R^1$ is hydrogen or $C_{1-6}$alkyl, and $R^2$ is —$(CH_2)_r$—Y—$R^h$.

In certain embodiments of formula IV or formula V, $R^1$ is hydrogen or $C_{1-6}$alkyl, $R^2$ is —$(CH_2)_r$—Y—$R^h$, and Y is —C(O)—.

In certain embodiments of formula IV or formula V, $R^1$ is hydrogen or $C_{1-6}$alkyl, $R^2$ is —$(CH_2)_r$—Y—$R^h$, Y is —C(O)—, and r is 1.

In certain embodiments of formula IV or formula V, $R^1$ is hydrogen or $C_{1-6}$alkyl, $R^2$ is —$(CH_2)_r$—Y—$R^h$, Y is —C(O)—, r is 1, and $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino.

In certain embodiments of formula IV or formula V, $R^1$ is hydrogen or $C_{1-6}$alkyl, $R^2$ is —$(CH_2)_r$—Y—$R^h$, Y is —C(O)—, r is 1, $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$ alkylamino, p is 0 or 1, q is 0 or 1, and $R^5$ and $R^6$ are halo.

In certain embodiments of formula IV or formula V, $R^1$ is hydrogen or $C_{1-6}$alkyl, $R^2$ is —$(CH_2)_r$—Y—$R^h$, Y is —C(O)—, and r is 0.

In certain embodiments of formula IV or formula V, n is 1, $R^1$ is hydrogen or $C_{1-6}$alkyl, $R^2$ is $(CH_2)_r$—Y—$R^h$, Y is —C(O)—, r is 0, and $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino.

In certain embodiments of formula IV or formula V, $R^1$ is hydrogen or $C_{1-6}$alkyl, $R^2$ is —$(CH_2)_r$—Y—$R^h$, Y is —C(O)—, r is 0, $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino, p is 0 or 1, q is 0 or 1, and $R^5$ and $R^6$ are halo.

In certain embodiments of formula IV or formula V, $R^1$ is hydrogen or $C_{1-6}$alkyl, $R^2$ is —$(CH_2)_r$—Y—$R^h$, and Y is —$SO_2$—.

In certain embodiments of formula IV or formula V, $R^1$ is hydrogen or $C_{1-6}$alkyl, $R^2$ is —$(CH_2)_r$—Y—$R^h$, Y is —$SO_2$—, and r is 1.

In certain embodiments of formula IV or formula V, $R^1$ is hydrogen or $C_{1-6}$alkyl, $R^2$ is —$(CH_2)_r$—Y—$R^h$, Y is —$SO_2$—, r is 1, and $R^h$ is $C_{1-6}$alkyl, $C_{3-8}$cycloalkyl, $C_{1-6}$alkoxy, halo-$C_{1-6}$alkyl, amino, N—$C_{1-6}$alkylamino or N,N-di-$C_{1-6}$alkylamino.

In certain embodiments of formula IV or formula V, $R^1$ is hydrogen or $C_{1-6}$alkyl, $R^2$ is —$(CH_2)_r$—Y—$R^h$, Y is —$SO_2$—, r is 1, $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino, p is 0 or 1, q is 0 or 1, and $R^5$ and $R^6$ are halo.

In certain embodiments of formula IV or formula V, $R^1$ is hydrogen or $C_{1-6}$alkyl, $R^2$ is —$(CH_2)_r$—Y—$R^h$, Y is —$SO_2$—, and r is 0.

In certain embodiments of formula IV or formula V, $R^1$ is hydrogen or $C_{1-6}$alkyl, $R^2$ is —$(CH_2)_r$—Y—$R^h$, Y is —$SO_2$—, r is 0, and $R^h$ is $C_{1-6}$alkyl, $C_{3-8}$ cycloalkyl, $C_{1-6}$alkoxy, halo-$C_{1-6}$alkyl, amino, N—$C_{1-6}$alkylamino or N,N-di-$C_{1-6}$alkylamino.

In certain embodiments of formula IV or formula V, $R^1$ is hydrogen or $C_{1-6}$alkyl, $R^2$ is —$(CH_2)_r$—Y—$R^h$, Y is —$SO_2$—, r is 0, $R^h$ is $C_{1-6}$alkyl, $C_{3-8}$cycloalkyl, $C_{1-6}$alkoxy, halo-$C_{1-6}$alkyl, amino, N—$C_{1-6}$alkylamino or N,N-di-$C_{1-6}$alkylamino, p is 0 or 1, q is 0 or 1, and $R^5$ and $R^6$ are halo.

In certain embodiments of the invention, the compounds are of formula VI:

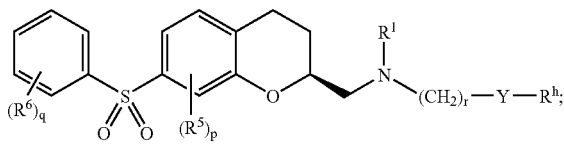

VI wherein:
p and q each independently is from 0 to 2;
r is 0 or 1;
Y is —C(O)— or —$SO_2$—;
$R^1$ is hydrogen or $C_{1-6}$alkyl; and
$R^5$, $R^6$ and $R^h$ are as defined herein.

In certain embodiments of the invention, the compounds are of formula VII:

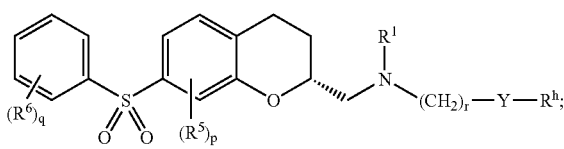

VII wherein:
p and q each independently is from 0 to 2;
$R^1$ is hydrogen or $C_{1-6}$alkyl; and
r, Y, $R^5$, $R^6$ and $R^h$ are as defined herein.

In certain embodiments of the invention, the compounds are of formula VIII:

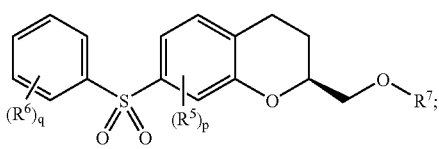

VIII wherein:
$R^7$ is:
hydrogen;
$C_{1-6}$alkyl;
$C_{3-8}$ cycloalkyl
hetero-$C_{1-6}$alkyl;
halo-$C_{1-6}$alkyl; or
—$(CH_2)_r$—Y—$R^h$; and p, q, r, Y, $R^5$, $R^6$ and $R^h$ are as defined herein.

In certain embodiments of the invention, the compounds are of formula IX:

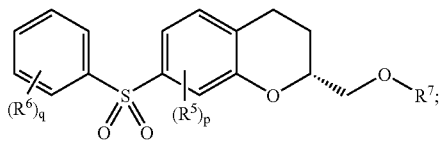

IX wherein:
$R^7$ is:
hydrogen;
$C_{1-6}$alkyl;
$C_{3-8}$ cycloalkyl
hetero-$C_{1-6}$alkyl;
halo-$C_{1-6}$alkyl; or
—$(CH_2)_r$—Y—$R^h$; and p, q, r, Y, $R^5$, $R^6$ and $R^h$ are as defined herein.

In certain embodiments of formula VIII or formula IX, $R^7$ is hydrogen or $C_{1-6}$alkyl.

Where any of $R^1$, $R^2$, $R^3$, $R^4$, $R^5$, $R^6$, $R^a$, $R^b$, $R^c$, $R^d$, $R^e$, $R^f$, $R^g$ or $R^h$ are alkyl or contain an alkyl moiety, such alkyl is preferably lower alkyl, i.e. $C_1$-$C_6$alkyl, and more preferably $C_1$-$C_4$alkyl.

In any of the embodiments of formula IV and formula IV, when $R^1$ or $R^2$ is $C_{1-6}$alkyl, it is preferably methyl.

Representative compounds in accordance with the invention are shown in Table 1.

TABLE 1

| # | Structure | Name (Autonom) | MP |
|---|---|---|---|
| 1 | 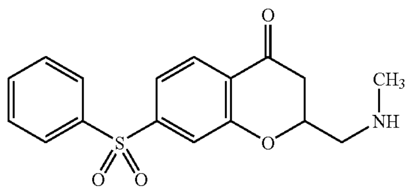 | 7-Benzenesulfonyl-2-methylaminomethyl-chroman-4-one | 157.8-189.6° C. (TFA Salt) |
| 2 | 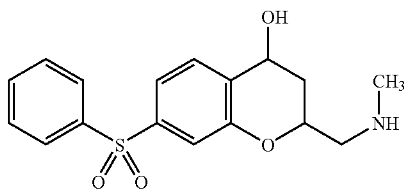 | 7-Benzenesulfonyl-2-methylaminomethyl-chroman-4-ol | 165.4-167.3° C. (TFA Salt) |
| 3 | 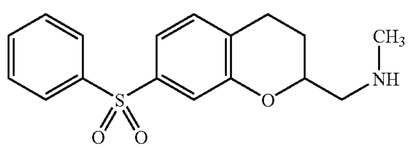 | (7-Benzenesulfonyl-chroman-2-ylmethyl)-methyl-amine | 196.2-198.2° C. (TFA Salt) |
| 4 | 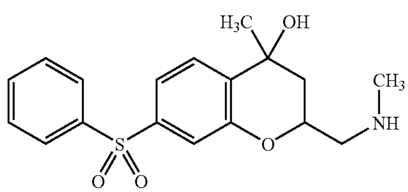 | 7-Benzenesulfonyl-4-methyl-2-methylaminomethyl-chroman-4-ol | 163.9-165.3° C. |
| 5 | 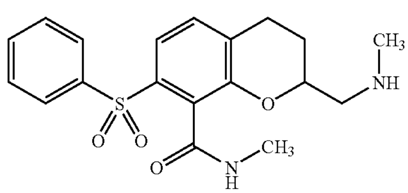 | 7-Benzenesulfonyl-2-methylaminomethyl-chroman-8-carboxylic acid methylamide | 375 |
| 6 | 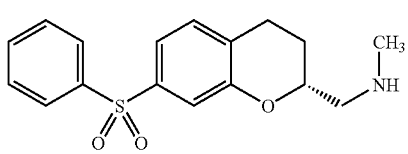 | (R)-(7-Benzenesulfonyl-chroman-2-ylmethyl)-methyl-amine | 271.8-273.0° C. (HCl Salt) |
| 7 | 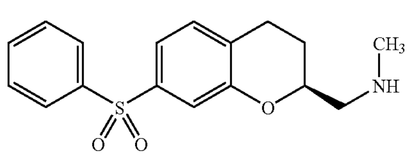 | (S)-(7-Benzenesulfonyl-chroman-2-ylmethyl)-methyl-amine | 270.0-270.4° C. (HCl Salt) |
| 8 | 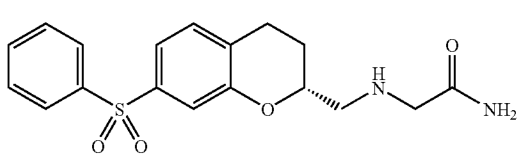 | (R)-2-[(7-Benzenesulfonyl-chroman-2-ylmethyl)-amino]-acetamide | 361 |

TABLE 1-continued

| # | Structure | Name (Autonom) | MP |
|---|---|---|---|
| 9 | 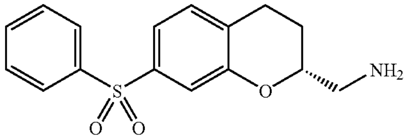 | (R)-C-(7-Benzenesulfonyl-chroman-2-yl)-methylamine | 304 |
| 10 | 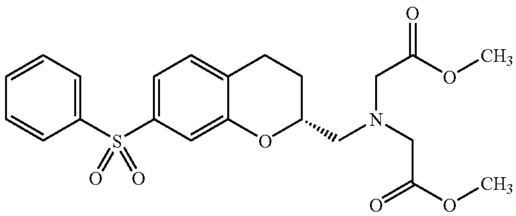 | (R)-[(7-Benzenesulfonyl-chroman-2-ylmethyl)-methoxycarbonylmethyl-amino]-acetic acid methyl ester | 448 |
| 11 | 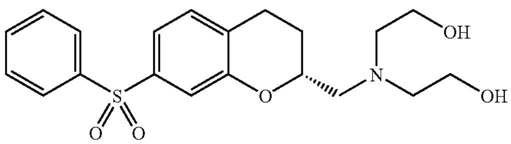 | (R)-2-[(7-Benzenesulfonyl-chroman-2-ylmethyl)-(2-hydroxy-ethyl)-amino]-ethanol | 392 |
| 12 | 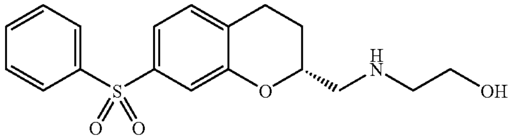 | 2-[(7-Benzenesulfonyl-chroman-2-ylmethyl)-amino]-ethanol | 348 |
| 13 | 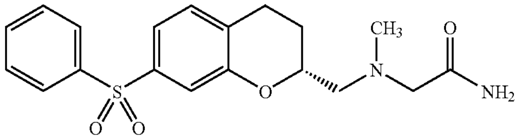 | (R)-2-[(7-Benzenesulfonyl-chroman-2-ylmethyl)-methyl-amino]-acetamide | 375 |
| 14 | 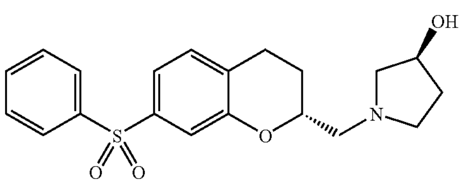 | (R)-1-(7-Benzenesulfonyl-chroman-2-ylmethyl)-pyrrolidin-(R)-3-ol | 374 |
| 15 | 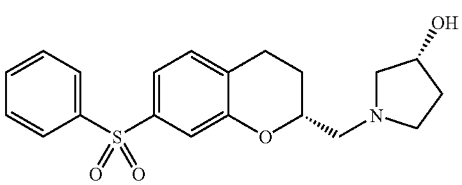 | (R)-1-(7-Benzenesulfonyl-chroman-2-ylmethyl)-pyrrolidin-(S)-3-ol | 374 |
| 16 | 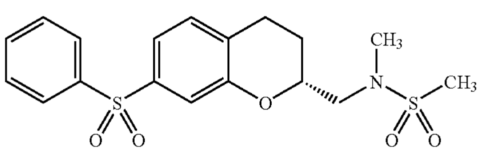 | (R)-N-(7-Benzenesulfonyl-chroman-2-ylmethyl)-N-methyl-methanesulfonamide | 396 |
| 17 | 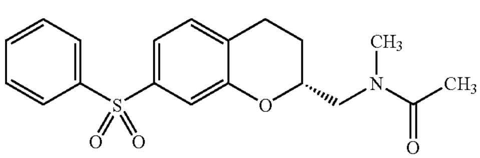 | (R)-N-(7-Benzenesulfonyl-chroman-2-ylmethyl)-N-methyl-acetamide | 360 |

TABLE 1-continued

| # | Structure | Name (Autonom) | MP |
|---|---|---|---|
| 18 | 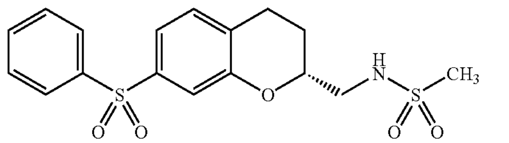 | (R)-N-(7-Benzenesulfonyl-chroman-2-ylme\thyl)-methanesulfonamide | 382 |
| 19 | 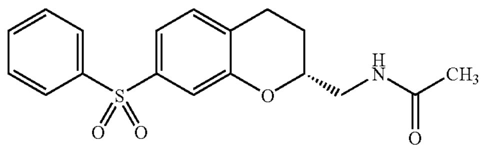 | (R)-N-(7-Benzenesulfonyl-chroman-2-ylmethyl)-acetamide | 346 |
| 20 | 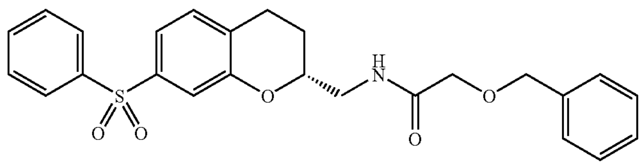 | (R)-N-(7-Benzenesulfonyl-chroman-2-ylmethyl)-2-benzyloxy-acetamide | 452 |
| 21 | 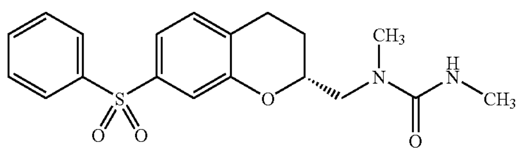 | (R)-1-(7-Benzenesulfonyl-chroman-2-ylmethyl)-1,3-dimethyl-urea | 375 |
| 22 | 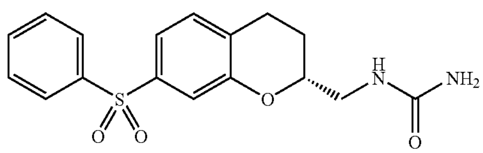 | (R)-(7-Benzenesulfonyl-chroman-2-ylmethyl)-urea | 347 |
| 23 | 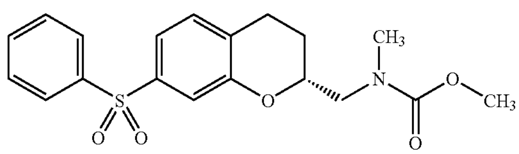 | (R)-(7-Benzenesulfonyl-chroman-2-ylmethyl)-methyl-carbamic acid methyl ester | 390 |
| 24 | 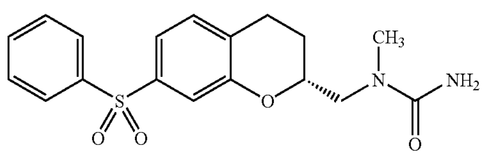 | (R)-1-(7-Benzenesulfonyl-chroman-2-ylmethyl)-1-methyl-urea | 361 |
| 25 | 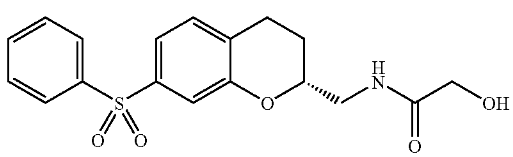 | (R)-N-(7-Benzenesulfonyl-chroman-2-ylmethyl)-2-hydroxy-acetamide | 362 |
| 26 | 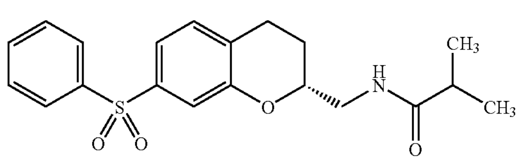 | (R)-N-(7-Benzenesulfonyl-chroman-2-ylmethyl)-isobutyramide | 374 |

TABLE 1-continued

| # | Structure | Name (Autonom) | MP |
|---|---|---|---|
| 27 | 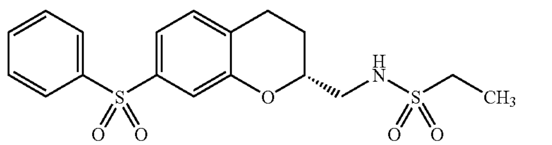 | (R)-Ethanesulfonic acid(7-benzenesulfonyl-chroman-2-ylmethyl)-amide | 396 |
| 28 | 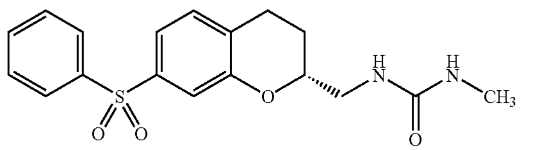 | (R)-1-(7-Benzenesulfonyl-chroman-2-ylmethyl)-3-methyl-urea | 361 |
| 29 | 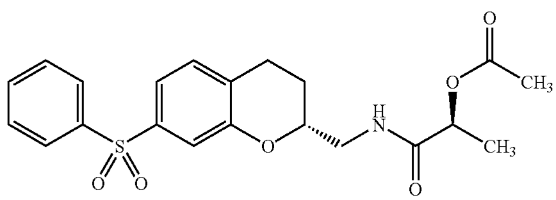 | (R)-Acetic acid 1-[(7-benzenesulfonyl-chroman-2-ylmethyl)-carbamoyl]-ethyl ester | 418 |
| 30 | 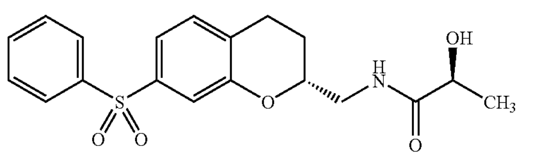 | (R)-N-(7-Benzenesulfonyl-chroman-2-ylmethyl)-2-hydroxy-propionamide | 129.5-131.5° C. |
| 31 | 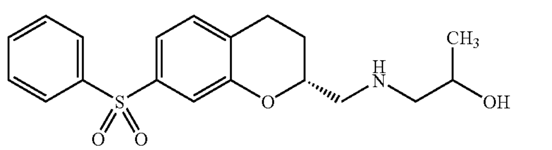 | (R)-1-[(7-Benzenesulfonyl-chroman-2-ylmethyl)-amino]-propan-2-ol | 362 |
| 32 | 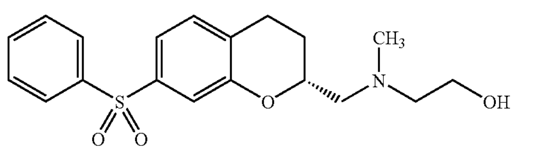 | (R)-2-[(7-Benzenesulfonyl-chroman-2-ylmethyl)-methyl-amino]-ethanol | 362 |
| 33 | 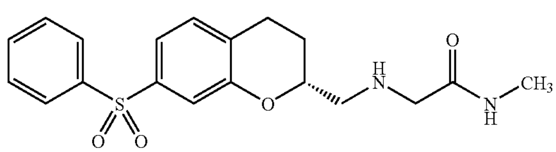 | (R)-2-[(7-Benzenesulfonyl-chroman-2-ylmethyl)-amino]-N-methyl-acetamide | 375 |
| 34 | 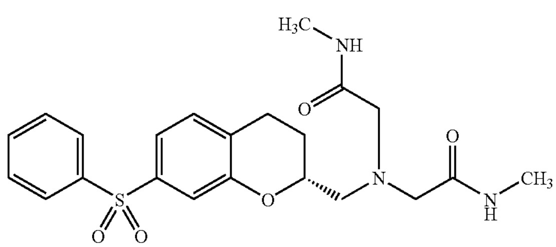 | (R)-2-[(7-Benzenesulfonyl-chroman-2-ylmethyl)-methylcarbamoylmethyl-amino]-N-methyl-acetamide | 446 |
| 35 | 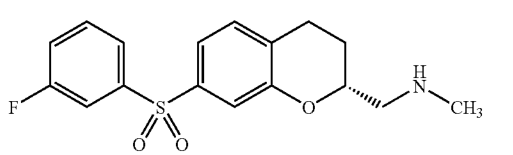 | (R)-[7-(3-Fluoro-benzenesulfonyl)-chroman-2-ylmethyl]-methyl-amine | 259.0-261.0° C. |

TABLE 1-continued

| # | Structure | Name (Autonom) | MP |
|---|---|---|---|
| 36 | 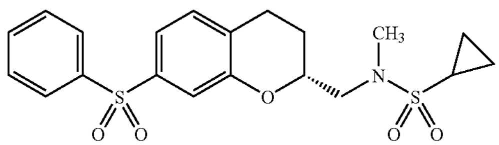 | (R)-Cyclopropanesulfonic acid(7-benzenesulfonyl-chroman-2-ylmethyl)-methyl-amide | 422 |
| 37 | 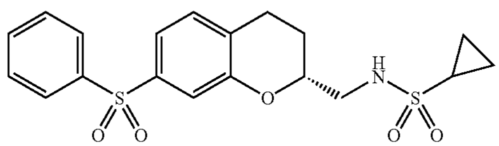 | (R)-Cyclopropanesulfonic acid(7-benzenesulfonyl-chroman-2-ylmethyl)-amide | 408 |
| 38 | 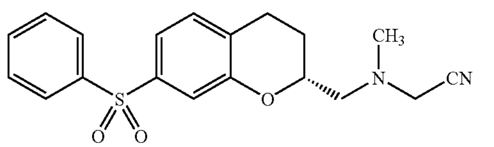 | (R)-[(7-Benzenesulfonyl-chroman-2-ylmethyl)-methyl-amino]-acetonitrile | 343 |
| 39 | 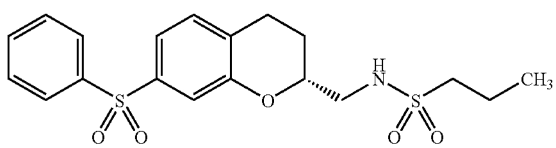 | (R)-Propane-1-sulfonic acid(7-benzenesulfonyl-chroman-2-ylmethyl)-amide | 410 |
| 40 | 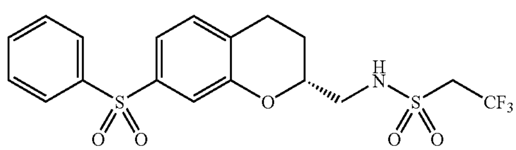 | (R)-2,2,2-Trifluoro-ethanesulfonic acid (7-benzenesulfonyl-chroman-2-ylmethyl)-amide | 450 |
| 41 | 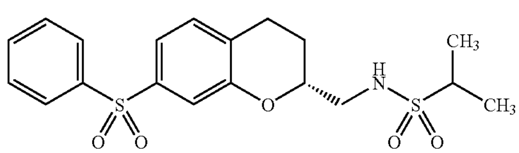 | (R)-Propane-2-sulfonic acid(7-benzenesulfonyl-chroman-2-ylmethyl)-amide | 410 |
| 42 | 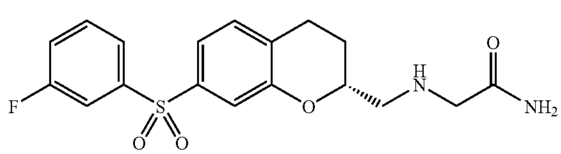 | (R)-2-{[7-(3-Fluoro-benzenesulfonyl)-chroman-2-ylmethyl]-amino}-acetamide | 218.0–220.3° C. (HCl salt) |
| 43 | 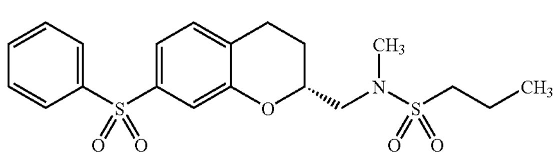 | (R)-Propane-1-sulfonic acid(7-benzenesulfonyl-chroman-2-ylmethyl)-methyl-amide | 424 |
| 44 | 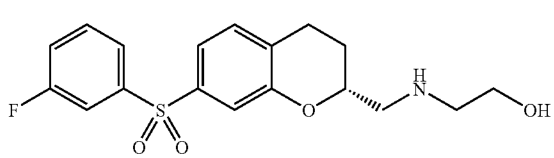 | (R)-2-{[7-(3-Fluoro-benzenesulfonyl)-chroman-2-ylmethyl]-amino}-ethanol | 226.1–228.3° C. |
| 45 | 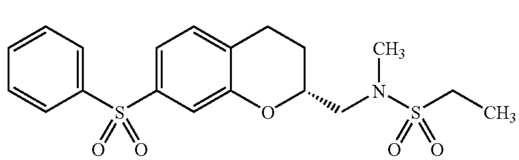 | (R)-Ethanesulfonic acid(7-benzenesulfonyl-chroman-2-ylmethyl)-methyl-amide | 410 |

TABLE 1-continued

| # | Structure | Name (Autonom) | MP |
|---|---|---|---|
| 46 | 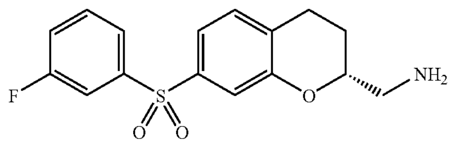 | (R)-C-[7-(3-Fluoro-benzenesulfonyl)-chroman-2-yl]-methylamine | 257.1–258.9° C. |
| 47 | 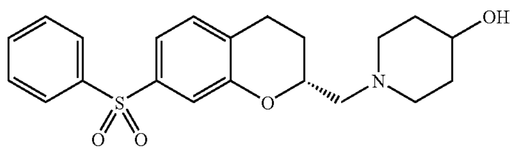 | (R)-1-(7-Benzenesulfonyl-chroman-2-ylmethyl)-piperidin-4-ol | 388 |
| 48 | 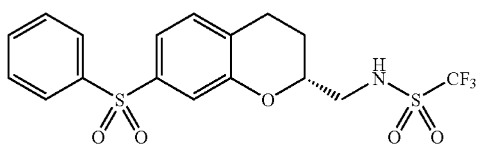 | (R)-N-(7-Benzenesulfonyl-chroman-2-ylmethyl)-C,C,C-trifluoro-methanesulfonamide | 436 |
| 49 | 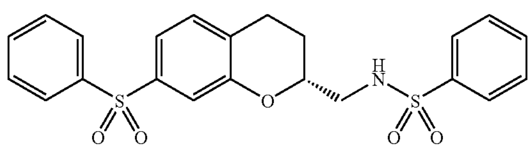 | (R)-N-(7-Benzenesulfonyl-chroman-2-ylmethyl)-benzenesulfonamide | 444 |
| 50 | 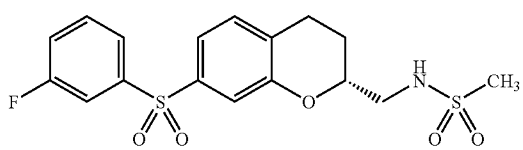 | (R)-N-[7-(3-Fluoro-benzenesulfonyl)-chroman-2-ylmethyl]-methanesulfonamide | 139.1-140.0° C. |
| 51 | 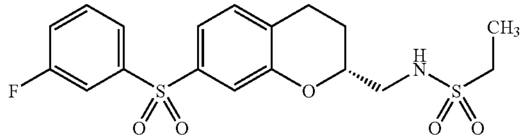 | (R)-Ethanesulfonic acid[7-(3-fluoro-benzenesulfonyl)-chroman-2-ylmethyl]-amide | 414 |
| 52 | 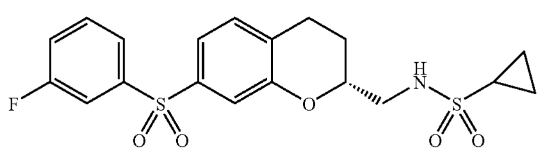 | (R)-Cyclopropanesulfonic acid[7-(3-fluoro-benzenesulfonyl)-chroman-2-ylmethyl]-amide | 426 |
| 53 | 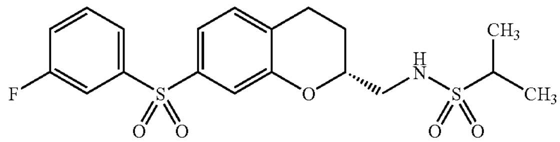 | (R)-Propane-2-sulfonic acid[7-(3-fluoro-benzenesulfonyl)-chroman-2-ylmethyl]-amide | 428 |
| 54 | 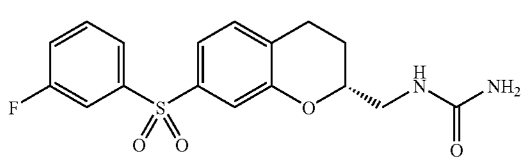 | (R)-[7-(3-Fluoro-benzenesulfonyl)-chroman-2-ylmethyl]-urea | 365 |
| 55 | 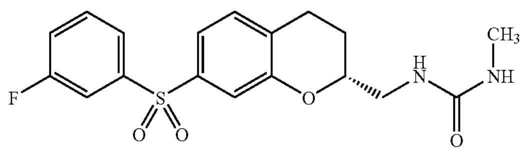 | (R)-1-[7-(3-Fluoro-benzenesulfonyl)-chroman-2-ylmethyl]-3-methyl-urea | 379 |

TABLE 1-continued

| # | Structure | Name (Autonom) | MP |
|---|---|---|---|
| 56 | 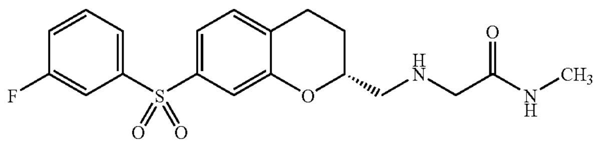 | (R)-2-{[7-(3-Fluoro-benzenesulfonyl)-chroman-2-ylmethyl]-amino}-N-methyl-acetamide | 393 |
| 57 | 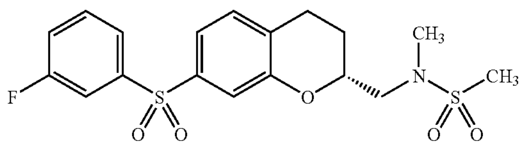 | (R)-N-[7-(3-Fluoro-benzenesulfonyl)-chroman-2-ylmethyl]-N-methyl-methanesulfonamide | 414 |
| 58 | 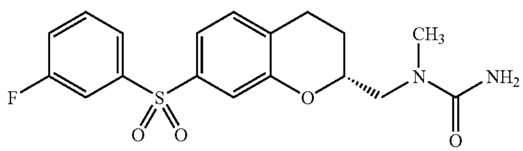 | (R)-1-[7-(3-Fluoro-benzenesulfonyl)-chroman-2-ylmethyl]-1-methyl-urea | 379 |
| 59 | 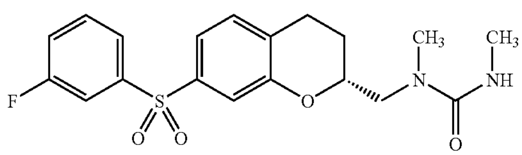 | (R)-1-[7-(3-Fluoro-benzenesulfonyl)-chroman-2-ylmethyl}-1,3-dimethyl-urea | 393 |
| 60 | 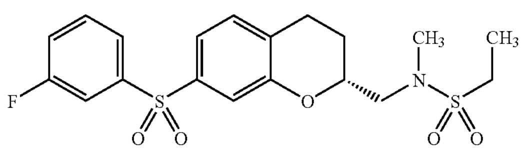 | (R)-Ethanesulfonic acid[7-(3-fluoro-benzenesulfonyl)-chroman-2-ylmethyl]-methyl-amide | 427 |
| 61 | 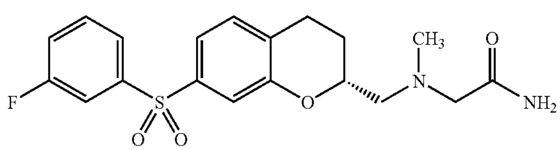 | (R)-2-{[7-(3-Fluoro-benzenesulfonyl)-chroman-2-ylmethyl]-methyl-amino}-acetamide | 393 |
| 62 | 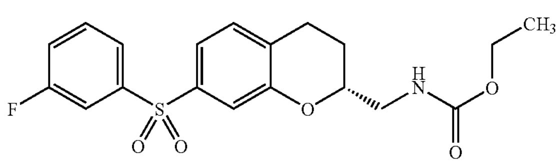 | (R)-[7-(3-Fluoro-benzenesulfonyl)-chroman-2-ylmethyl]-carbamic acid ethyl ester | 394 |
| 63 | 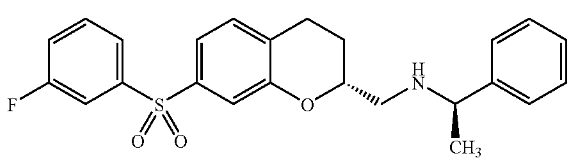 | (R)-[7-(3-Fluoro-benzenesulfonyl)-chroman-2-ylmethyl]-(1-(R)-phenyl-ethyl)-amine | 426 |
| 64 | 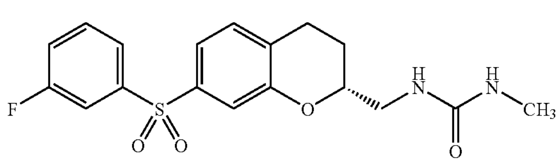 | (R)-1-[7-(3-Fluoro-benzenesulfonyl)-chroman-2-ylmethyl]-3-methyl-urea | 393 |

TABLE 1-continued

| # | Structure | Name (Autonom) | MP |
|---|---|---|---|
| 65 | 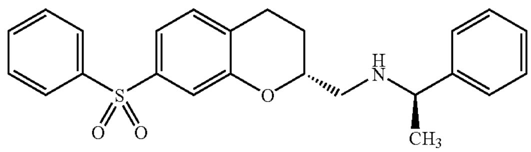 | (R)-(7-Benzenesulfonyl-chroman-2-ylmethyl)-(1-phenyl-ethyl)-amine | 408 |
| 66 | 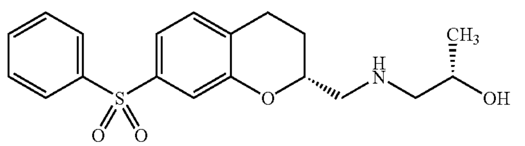 | (R)-1-[(7-Benzene sulfonyl-chroman-2-ylmethyl)-amino]-(S)-propan-2-ol | 362 |
| 67 | 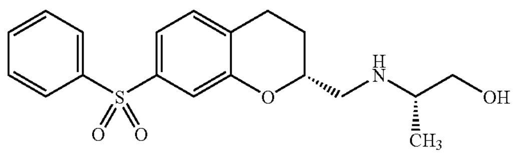 | (R)-2-[(7-Benzenesulfonyl-chroman-2-ylmethyl)-amino]-(R)-propan-1-ol | 362 |
| 68 | 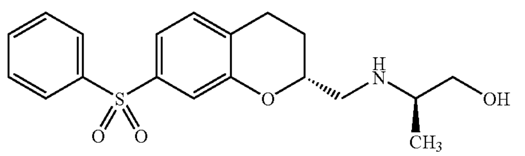 | (R)-2-[(7-Benzenesulfonyl-chroman-2-ylmethyl)-amino]-(S)-propan-1-ol | 362 |
| 69 | 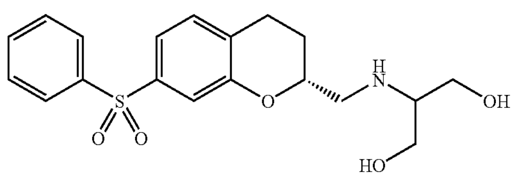 | (R)-2-[(7-Benzenesulfonyl-chroman-2-ylmethyl)-amino]-propane-1,3-diol | 378 |
| 70 | 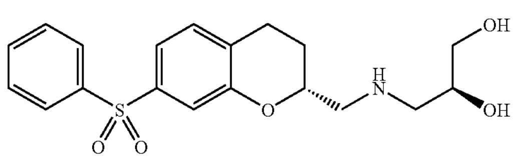 | (R)-3-[(7-Benzenesulfonyl-chroman-2-ylmethyl)-amino]-(R)-propane-1,2-diol | 378 |
| 71 | 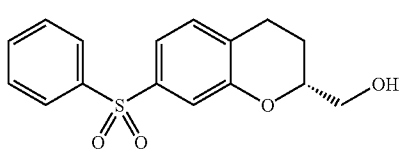 | (R)-(7-Benzenesulfonyl-chroman-2-yl)-methanol | 305 |
| 72 | 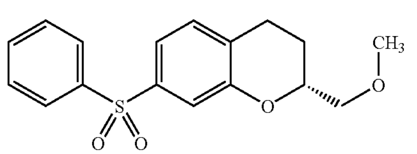 | (R)-7-Benzenesulfonyl-2-methoxymethyl-chroman | 319 |

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare compounds of the invention, wherein n, p, Ar, $R^1$, $R^2$, $R^3$, $R^4$ and $R^5$ are as defined herein.

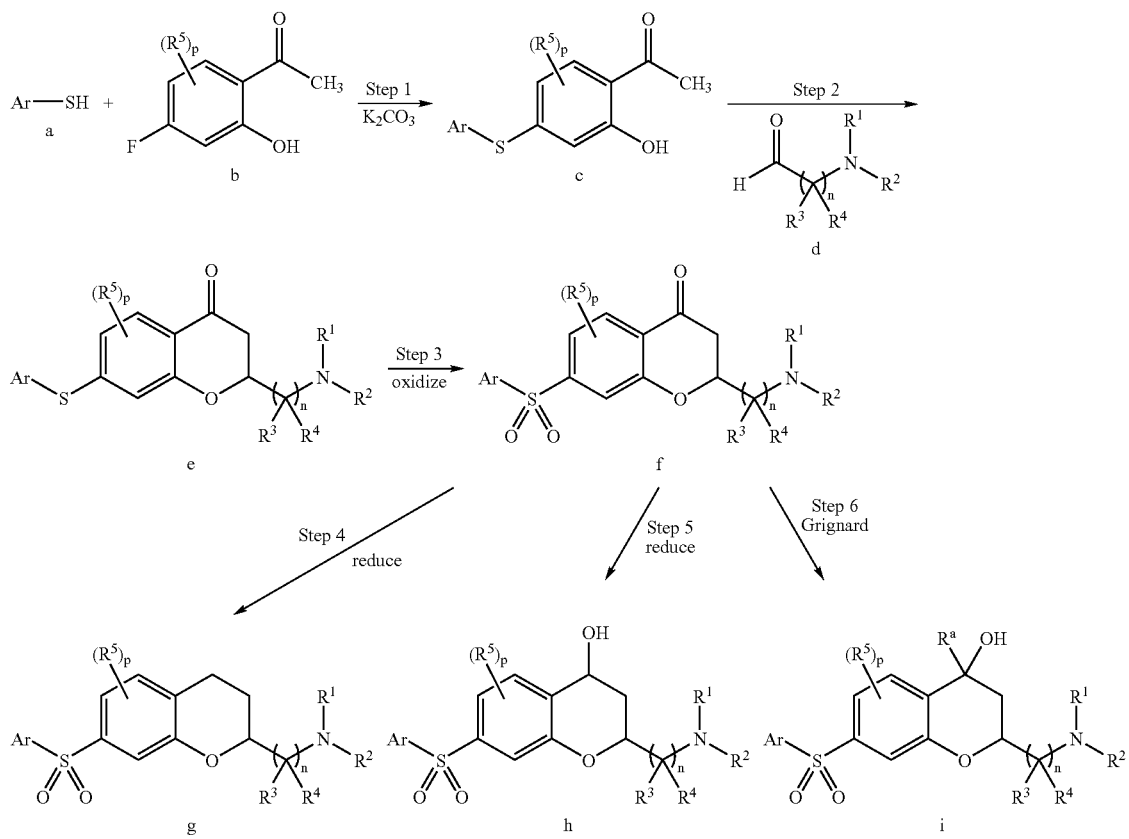

SCHEME A

In Step 1 of Scheme A, arylthiol compound a is reacted with acetyl fluorophenol b in the presence mild base such as potassium carbonate, to provide an arylsulfanyl phenol compound c. Compound c is then treated with amino aldehyde d in step 2 to afford arylsulfanyl chromanone e. In step 3 the sulfanyl group of compound e is oxidized to yield arylsulfonyl chromanone f. Compound f can undergo reduction in step 4 to convert the carbonyl group of compound f to a methylene group and thus provide an arylsulfonyl chroman compound g. The reduction of step 4 may be carried out, for example, by hydrogenation in the presence of $Pd(OH)_2$ catalyst under acidic conditions. Alternatively, following step 5 under different reducing conditions such as hydrogenation in the presence of Pd/C, a hydroxychroman compound h may be obtained. In yet another alternative, a Grignard reaction may be carried out in step 6 with alkyl Grignard reagent $R^aMgX$ ($R^a$ is alkyl and X is halo), to afford compound i. Compounds g, h, and i are compounds of formula I in accordance with the invention.

Many variations are possible in the procedure of Scheme A. For example, one of $R^1$ and $R^2$ may be a protecting group that is removed following step 4, 5 or 6. Further reaction of the group —NR¹R² may be carried out after step 4, 5 or 6. The oxidation of step 3 may be omitted to provide compounds where m is 0, or oxidation conditions may be varied to provide compounds where m is 1.

Scheme B below illustrates another synthetic procedure that may be used in preparation of compounds of the invention, wherein specific stereochemistry may be provided in the final product. The variables p, Ar, R¹, R² and R⁵ are as defined herein.

SCHEME B

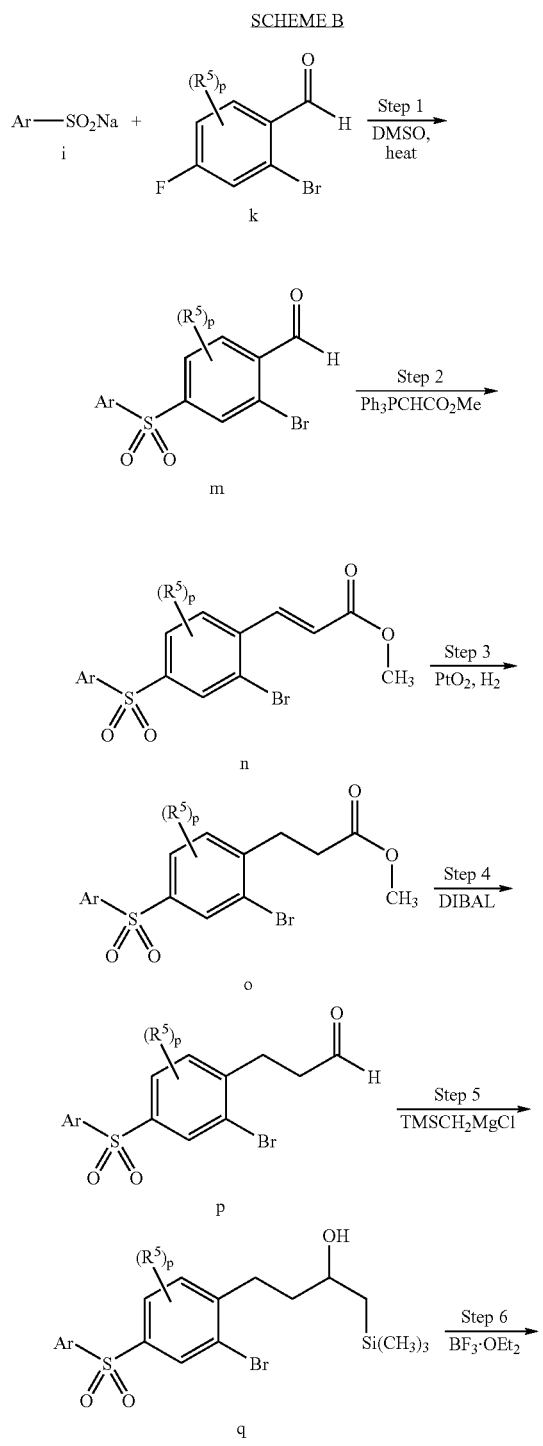

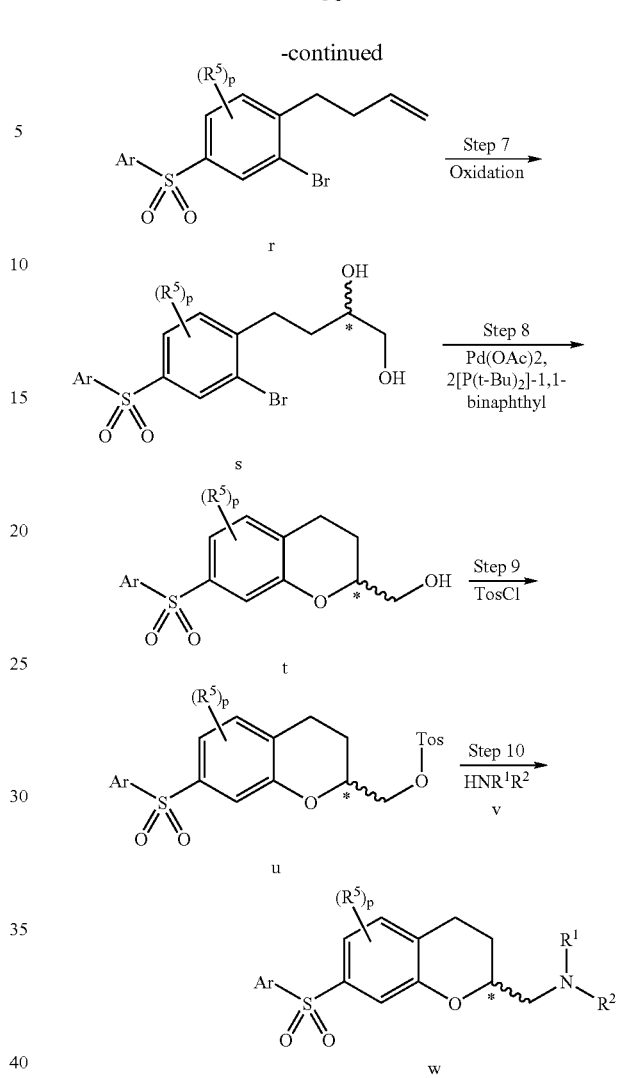

In step 1 of Scheme B, sodium arylsulfinate j and fluorobenzaldehyde k are reacted to form arylsulfonyl benzaldehyde m. Compound m is treated in step 2 with methyl triphenylphosphoanylidine acetate to afford cinnamate compound n. In step 3 cinnamate n is treated with hydrogen in the presence of platinum dioxide to give the corresponding aryl priopionate compound o. Propionate o undergoes reduction in step 4 by treatment with diisobutyl aluminum hydride or like hydride reducing agent to afford aldehyde compound p. In step 5 aldehyde p is reacted with trimethylsilylmethyl magnesium chloride to afford trimethylsilyl compound q. In step 6 compound q is treated with boron trifluoride etherate to give butenyl compound r.

In step 7 compound r undergoes an enantioselective oxidation reaction in the presence of potassium osmate to yield diol compound s When the reaction of step 7 is carried out in the presence of hydroquinidine(anthraquinone-1,4-dyl)ether, one specific stereoisomer of the chiral center indicated by the asterix is obtained. Carrying out the oxidation of step 7 in the presence of hydroquinine(anthraquinone-1,4-dyl)ether yields the other stereoisomer, as shown in the Examples below.

In step 8, a ring closure is effected by treatment of diol s with palladium diacetate in the presence of 2[P(t-Bu)₂]-1,1-binaphthyl, to afford chroman compound t. Chroman t is treated with tosyl chloride to form chroman tosylate u in step 9. In step 10, tosylate u is reacted with amine v to afford chroman w, which is a compound of formula I in accordance with the invention.

Many variations on the procedure of Scheme B are possible. In one such variation, tosyl chloride in step 9 is replaced with sodium azide to form the corresponding azido compound, which may then be reduced provide compound w wherein $R^1$ and $R^2$ are hydrogen.

Where $R^1$ and $R^2$ are hydrogen, the amino functionality of the compounds of the invention may be subject to various reactions to afford monoalkylamino, dialkylamino, amidinyl, guanidinyl, imidazolinyl, imidazolinylamino, sulfonamide, carboxamide, urea, carbamate and other functionalities as shown in Scheme C.

Utility

The compounds of the invention have selective affinity for 5-HT receptors, including the $5-HT_6$ the $5-HT_{2A}$ receptor, or both, and as such are expected to be useful in the treatment of certain CNS disorders such as Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also

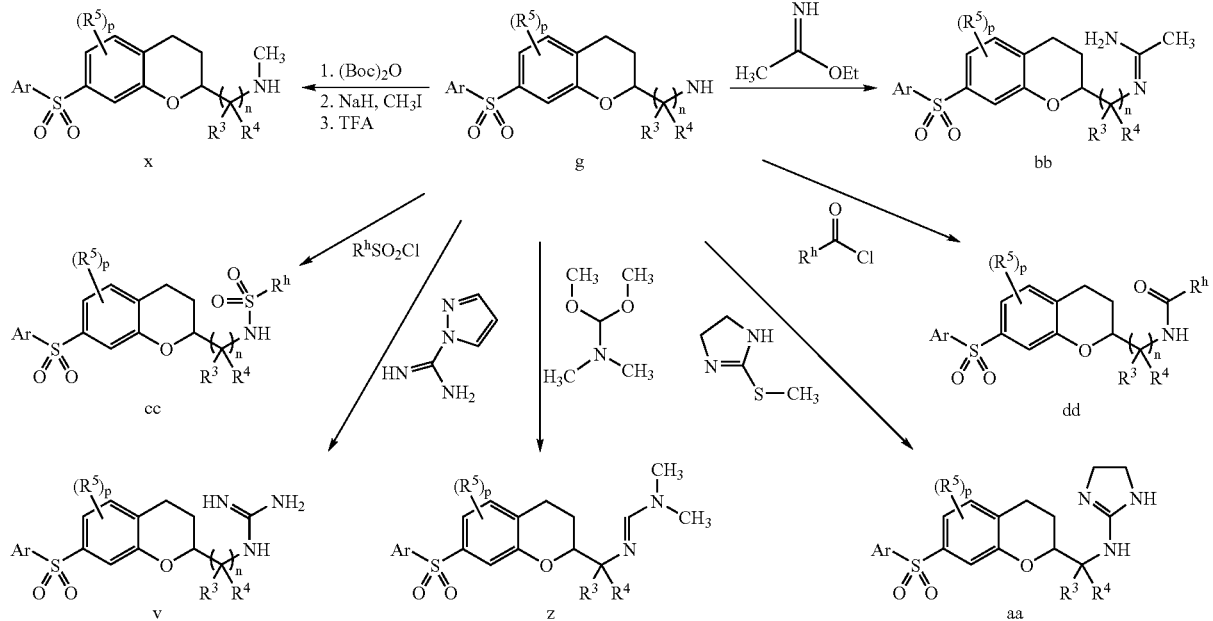

SCHEME C

In Scheme C, arylsulfonyl chroman compound g may be protected, subject to methylation under reducing conditions, and then deprotected to provide methylamino compound x. Compound x may then be subject to another alkylation (not shown) to provide the corresponding dimethylamino or other dialkylamino compound.

Compound g may also be reacted with 1H-pyrazol-1-carboxamidine hydrochloride in the presence of amine catalyst under polar aprotic solvent conditions to afford guanidine compound v. Alternatively, compound g may be reacted with dimethylformamide dimethyl acetal to yield formamidine compound z. As yet another alternative, compound g may be treated with 2-methylsulfanyl-4,5-dihydro-1H-imidazole to afford imidazolinylamino compound aa. In still another alternative, compound g may be reacted with ethyl imidate (acetimidic acid ethyl ester) to provide acetamidine compound bb. In yet other alternatives, compound g may be treated with a sulfonyl chloride to afford sulfonamide compound cc, or may be treated with an acyl chloride to afford compound dd.

Specific details for producing compounds of the invention are described in the Examples section below.

expected to be of use in the treatment of certain GI (gastrointestinal) disorders such functional bowel disorder and irritable bowel syndrome.

Testing

The pharmacology of the compounds of this invention was determined by art recognized procedures. The in vitro techniques for determining the affinities of test compounds at the 5-HT6 receptor and the 5-HT2A receptor in radioligand binding and functional assays are described below.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

EXAMPLES

The following preparations and examples are given to enable those skilled in the art to more clearly understand and to practice the present invention. They should not be considered as limiting the scope of the invention, but merely as being illustrative and representative thereof. The following abbreviations may be used in the Examples.

| ABBREVIATIONS | |
|---|---|
| DCM | dichloromethane/methylene chloride |
| DMF | N,N-dimethylformamide |
| DMAP | 4-dimethylaminopyridine |
| EtOAc | ethyl acetate |
| EtOH | ethanol |
| tBuOH | tert-butanol |
| gc | gas chromatography |
| HMPA | hexamethylphosphoramide |
| hplc | high performance liquid chromatography |
| mCPBA | m-chloroperbenzoic acid |
| MeCN | acetonitrile |
| MeOH | methanol |
| NMP | N-methyl pyrrolidinone |
| TEA | triethylamine |
| TFA | trifluoroacetic acid |
| THF | tetrahydrofuran |
| LDA | lithium diisopropylamine |
| TLC | thin layer chromatography |
| LAH | lithium aluminum hydride |

Example 1

7-Benzenesulfonyl-2-methylaminomethyl-chroman-4-one

The synthetic procedure of Example 1 is outlined in Scheme D below.

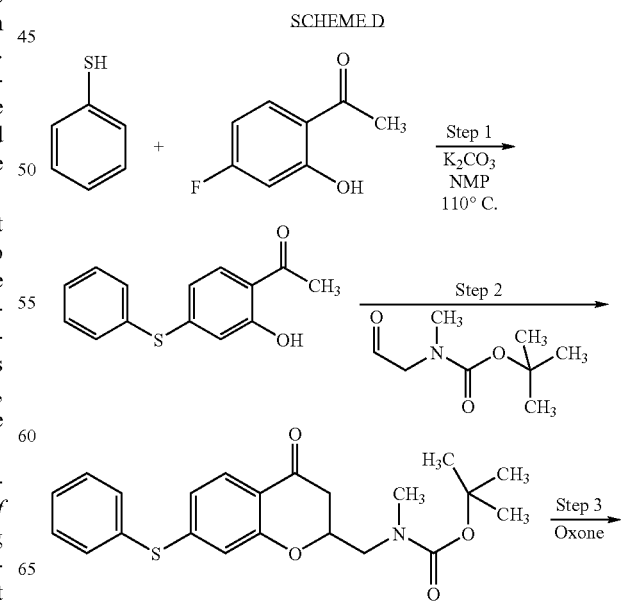

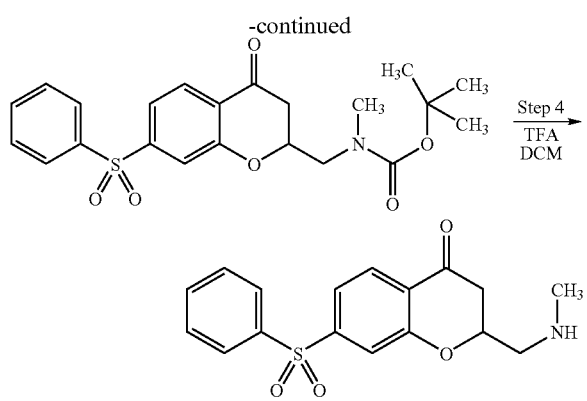

Step 1

1-(2-Hydroxy-4-phenylsulfanyl-phenyl)-ethanone

To a solution of 4-fluoro-2-hydroxyacetophenone (3.083 g, 20 mmol) in NMP (50 mL) were added thiophenol (2.054 ml, 20 mmol) and $K_2CO_3$ (8.293 g, 60 mmol). The reaction was heated at 110° C. overnight. Upon cooling the mixture was poured into water, acidified by addition of HCl (diluted) and extracted with $Et_2O$. The combined organic extracts were washed with water and brine, dried over $Na_2SO_4$, filtered and concentrated in vacuo to afford 1-(2-hydroxy-4-phenylsulfanyl-phenyl)-ethanone (4.980 g of oil) that was used for the next step without further purification.

Step 2

Methyl-(4-oxo-7-phenylsulfanyl-chroman-2-ylmethyl)-carbamic acid tert-butyl ester To a solution of 1-(2-hydroxy-4-phenylsulfanyl-phenyl)-ethanone (244 mg, 1 mmol) and methyl-(2-oxo-ethyl)-carbamic acid tert-butyl ester (259 mg, 1.5 mmol) (*Tetrahedron* 58, 2002, 1719-37) in toluene (25 mL) was added pyrrolidine (71 mg, 1 mmol). The reaction was stirred at room temperature for 60 hours. The mixture was concentrated in vacuo and the residue was purified via flash chromatography (hexane/$Et_2O$, 3/1) to give methyl-(4-oxo-7-phenylsulfanyl-chroman-2-ylmethyl)-carbamic acid tert-butyl ester (134 mg, 34% yield) as clear oil.

Step 3

(7-Benzenesulfonyl-4-oxo-chroman-2-ylmethyl)-methyl-carbamic acid tert-butyl ester To a solution of methyl-(4-oxo-7-phenylsulfanyl-chroman-2-ylmethyl)-carbamic acid tert-butyl ester (200 mg, 0.5 mmol) in a mixture acetonitrile/methanol/water (1/1/1, 30 mL) was added oxone (922 mg, 1.5 mmol), and the reaction was stirred at room temperature for 1 hour. The mixture was then diluted with water and the solid was filtered off. The filtrate was concentrated in vacuo to give (7-benzenesulfonyl-4-oxo-chroman-2-ylmethyl)-methyl-carbamic acid tert-butyl ester (186 mg, 86% yield) as yellow glass which was used without further purification for deprotection in the next step.

Step 4

7-Benzenesulfonyl-2-methylaminomethyl-chroman-4-one

To a solution of (7-benzenesulfonyl-4-oxo-chroman-2-yl)-methyl-carbamic acid tert-butyl ester (180 mg, 0.417 mmol) in DCM (20 mL) at room temperature was added TFA (5 drops). The reaction was stirred for 4 hours, then concentrated in vacuo. The residue was recrystallized from acetone/hexane to give 7-Benzenesulfonyl-2-methylaminomethyl-chroman-4-one (69 mg, 50% yield) as the trifluoroacetic acid salt; Mp 157.8-189.6° C.

Example 2

7-Benzenesulfonyl-2-methylaminomethyl-chroman-4-ol

The synthetic procedure of Example 1 is outlined in Scheme E below.

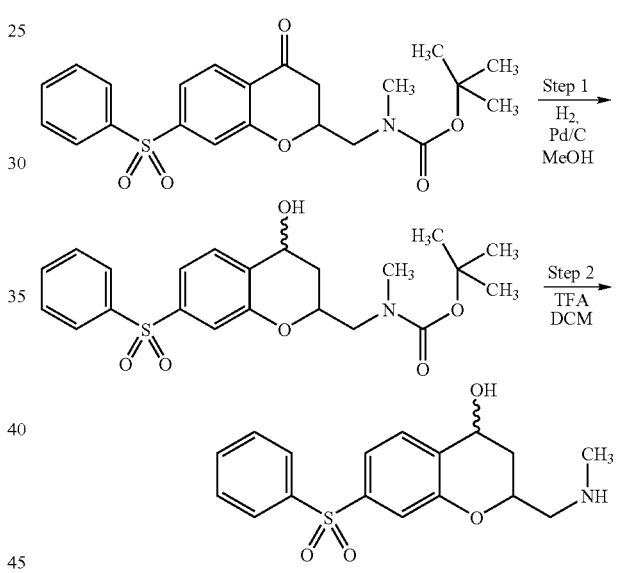

Step 1

(7-Benzenesulfonyl-4-hydroxy-chroman-2-ylmethyl)-methyl-carbamic acid tert-butyl ester To a solution of (7-benzenesulfonyl-4-oxo-chroman-2-ylmethyl)-methyl-carbamic acid tert-butyl ester (216 mg, 0.5 mmol) in MeOH (40 mL) was added Pd/C (10%, 20 mg) and the mixture was stirred under balloon pressure of $H_2$ overnight. The reaction was filtered through a celite pad and the filtrate was concentrated in vacuo. The residue was purified via flash chromatography (DCM/MeOH, 99/1) to give (7-benzenesulfonyl-4-hydroxy-chroman-2-ylmethyl)-methyl-carbamic acid tert-butyl ester (159 mg, 74% yield).

Step 2

7-Benzenesulfonyl-2-methylaminomethyl-chroman-4-ol

To a solution of (7-benzenesulfonyl-4-hydroxy-chroman-2-ylmethyl)-methyl-carbamic acid tert-butyl ester (154 mg, 0.355 mmol) in DCM (25 mL) was added TFA (0.5 mL). The reaction was stirred for 4 h at RT, then concentrated in vacuo. The residue was recrystallized from acetone/hexane plus 1 drop of EtOAc to give 7-benzenesulfonyl-2-methylamino-chroman-4-ol trifluoroacetate (74 mg, 63% yield) as white powder; Mp 165.4-167.3° C.

Example 3

(7-Benzenesulfonyl-chroman-2-ylmethyl)-methyl-amine

The synthetic procedure of Example 1 is outlined in Scheme F below.

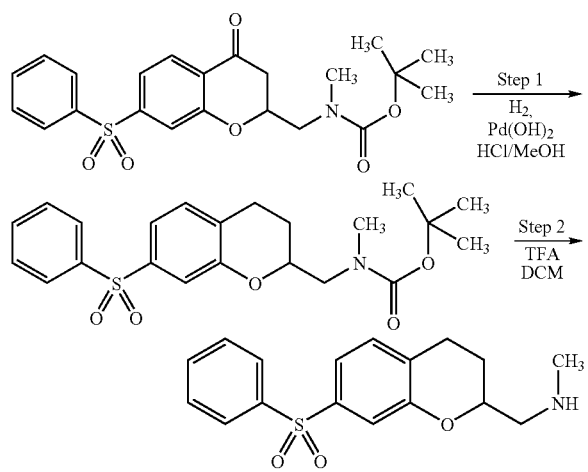

SCHEME F

Step 1

(7-Benzenesulfonyl-chroman-2-ylmethyl)-methyl-carbamic acid tert-butyl ester

To a solution of (7-benzenesulfonyl-4-oxo-chroman-2-ylmethyl)-methyl-carbamic acid tert-butyl ester (155 mg, 0.359 mmol) in MeOH (50 mL) were added Pd(OH)$_2$ (10 mg) and HCl (concentrated, 5 drops) the mixture was shaken into a Parr apparatus under H$_2$ atmosphere (50 PSI) for 3 hours. The reaction was filtered through a celite pad and the filtrate was neutralized with Na$_2$CO$_3$. The mixture was filtered and the filtrate was concentrated in vacuo. The residue purified via flash chromatography (DCM/MeOH, 99/1) to give (7-benzenesulfonyl-chroman-2-ylmethyl)-methyl-carbamic acid tert-butyl ester (147 mg, 98% yield) as a clear glass.

Step 2

(7-Benzenesulfonyl-chroman-2-ylmethyl)-methyl-amine

To a solution of (7-benzenesulfonyl-chroman-2-ylmethyl)-methyl-carbamic acid tert-butyl ester (125 mg, 0.299 mmol) in DCM (25 mL) was added TFA (0.5 mL). The reaction was stirred for 4 h at RT, then concentrated in vacuo. The residue was recrystallized from acetone/hexane plus 1 EtOAc to give (7-benzenesulfonyl-chroman-2-ylmethyl)-methyl-amine (76 mg, 80% yield) as white needles: Mp 196.2-198.2° C.

Example 4

7-Benzenesulfonyl-4-methyl-2-methylaminomethyl-chroman-4-ol

The synthetic procedure of Example 1 is outlined in Scheme G below.

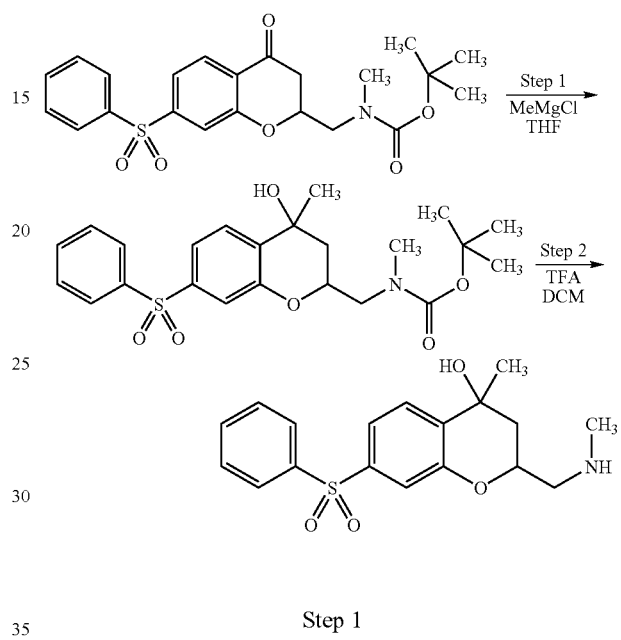

SCHEME G

Step 1

(7-Benzenesulfonyl-4-hydroxy-4-methyl-chroman-2-ylmethyl)-methyl-carbamic acid tert-butyl ester To a solution of (7-benzenesulfonyl-4-oxo-chroman-2-ylmethyl)-methyl-carbamic acid tert-butyl ester (216 mg, 0.5 mmol) in THF (25 mL) at 0° C. was added MeMgCl (3.0 M in THF, 0.208 mL). The mixture was allowed to warm at room temperature and was stirred for 6 hours. The reaction was quenched by addition of water and it was concentrated in vacuo. The aqueous residue was extracted with DCM and the organic extracts were dried over Na$_2$SO$_4$, filtered and concentrated in vacuo. The residue was purified via flash chromatography (DCM/MeOH, 97/3) to give (7-benzenesulfonyl-4-hydroxy-4-methyl-chroman-2-ylmethyl)-methyl-carbamic acid tert-butyl ester (214 mg, 96% yield) as yellow crystalline solid.

Step 2

7-Benzenesulfonyl-4-methyl-2-methylaminomethyl-chroman-4-ol

To a solution of (7-benzenesulfonyl-4-hydroxy-4-methyl-chroman-2-ylmethyl)-methyl-carbamic acid tert-butyl ester (212 mg, 0.474 mmol) in DCM (10 mL) was added TFA (1 mL). The reaction was stirred for 3 hours at room temperature, then concentrated in vacuo. The residue was purified via flash chromatography (DCM/MeOH/TEA) to give 7-benzenesulfonyl-4-methyl-2-methylaminomethyl-chroman-4-ol (63 mg, 38% yield) as a trifluoroacetate salt: Mp 163.9-165.3° C.

Example 5

7-Benzenesulfonyl-2-methylaminomethyl-chroman-8-carboxylic acid methylamide

The synthetic procedure of Example 1 is outlined in Scheme H below.

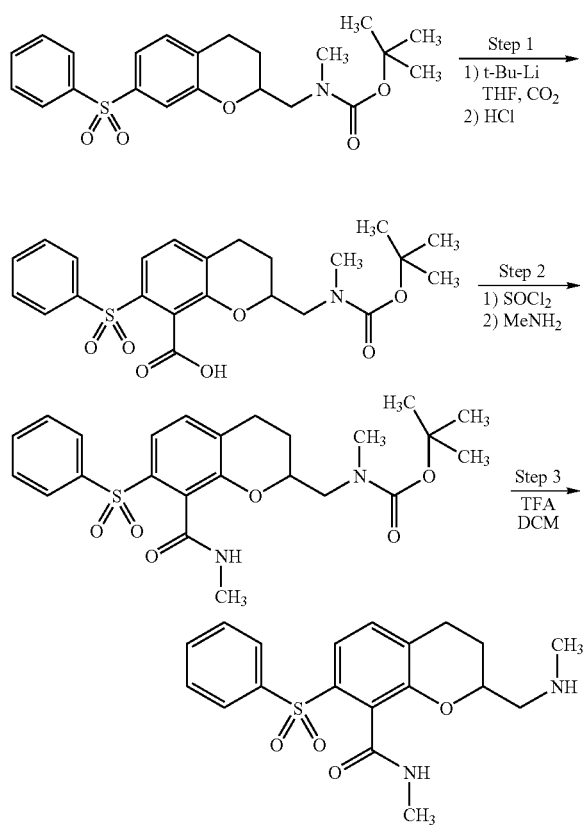

Step 1

7-Benzenesulfonyl-2-[(tert-butoxycarbonyl-methyl-amino)-methyl]-chroman-8-carboxylic acid To a solution of (7-benzenesulfonyl-4-oxo-chroman-2-ylmethyl)-methyl-carbamic acid tert-butyl ester (141 mg, 0.338 mmol) in THF (15 mL) cooled at −78° C. was added t-BuLi (1.7M in hexanes, 0.68 mL) dropwise. The reaction was allowed to warm to 0° C. for 3 hours, then it was quenched with $CO_2$ (gas) and diluted with water. The volatiles were removed in vacuo and the aqueous residue was washed with $Et_2O$ and then acidified to give a white precipitate that was filtered and dried to afford 7-benzenesulfonyl-2-[(tert-butoxycarbonyl-methyl-amino)-methyl]-chroman-8-carboxylic acid (55 mg, 35% yield) as a white powder.

Step 2

(7-Benzenesulfonyl-8-methylcarbamoyl-chroman-2-ylmethyl)-methyl-carbamic acid tert-butyl ester To a solution of 7-benzenesulfonyl-2-[(tert-butoxycarbonyl-methyl-amino)-methyl]-chroman-8-carboxylic acid (52 mg, 0.113 mmol) in DCM (10 mL) was added $SOCl_2$ (25 μL, 0.339 mmol). The reaction was heated to reflux for 2 hours, then a solution of $MeNH_2$ (40% in water, 0.5 mL) in acetonitrile (5 mL) was added and the mixture was allowed to stir for 1 hour. The reaction was concentrated in vacuo and the residue was purified via flash chromatography (DCM/MeOH, 98/2) to give (7-benzenesulfonyl-8-methylcarbamoyl-chroman-2-ylmethyl)-methyl-carbamic acid tert-butyl ester (52 mg, 98% yield) as clear oil.

Step 3

7-Benzenesulfonyl-2-methylaminomethyl-chroman-8-carboxylic acid methylamide

To a solution of (7-benzenesulfonyl-8-methylcarbamoyl-chroman-2-yl)-methyl-carbamic acid tert-butyl ester (52 mg, 0.109 mmol) in DCM (10 mL) was added TFA (0.5 mL) at RT. The reaction was stirred for 4 h and then it was concentrated in vacuo. The residue was purified via flash chromatography (DCM/MeOH/TEA) affording 7-benzenesulfonyl-2-methylaminomethyl-chroman-8-carboxylic acid methylamide (15 mg, 37% yield) as a tan oil; MS (M+H)=375.

Example 6

((R)-7-Benzenesulfonyl-chroman-2-ylmethyl)-methyl-amine

The synthetic procedure of Example 6 is outlined in Scheme I below.

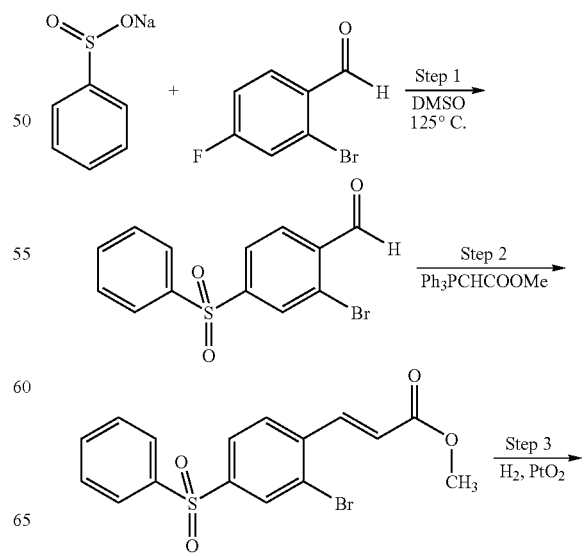

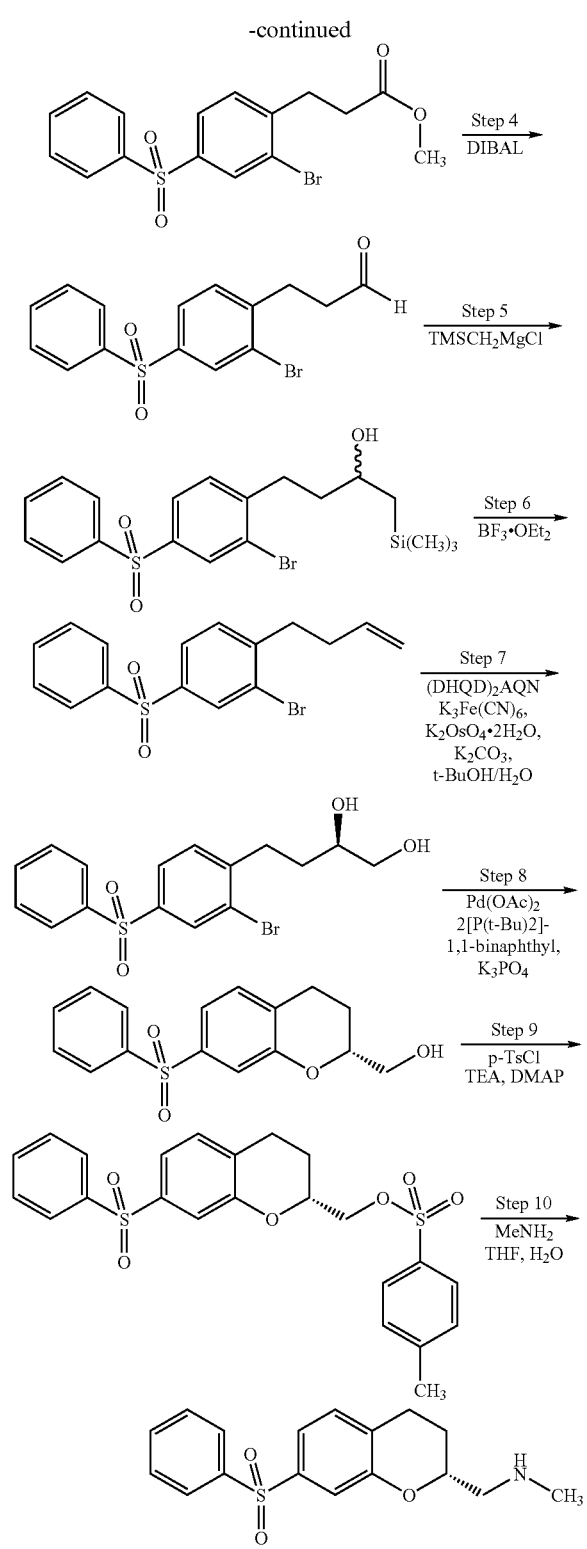

DMSO (100 mL) was heated at 125° C. overnight. Upon cooling the mixture was poured into water and extracted with EtOAc. The combined organic extracts were washed with water and brine, dried over $Na_2SO_4$, filtered and evaporated in vacuo. The residue was purified via flash chromatography (hexane/EtOAc, 4/1) to give 4-benzenesulfonyl-2-bromo-benzaldehyde (5.26 g, 32% yield) as white crystalline solid.

Step 2

(E)-3-(4-Benzenesulfonyl-2-bromo-phenyl)-acrylic acid methyl ester

To a solution of 4-benzenesulfonyl-2-bromo-benzaldehyde (7/47 g, 23.0 mmol) in toluene (100 mL) was added methyl(triphenylphosporanylidene)acetate (7.68 g, 23.0 mmol) under Ar atmosphere at RT. The mixture was stirred at room temperature overnight. The solvent was evaporated in vacuo and the residue was purified via flash chromatography (hexane/EtOAc) to afford (E)-3-(4-benzenesulfonyl-2-bromo-phenyl)-acrylic acid methyl ester (8.52 g) in mixture with some Z isomer.

Step 3

3-(4-Benzenesulfonyl-2-bromo-phenyl)-propionic acid methyl ester

To a solution of (E)-3-(4-benzenesulfonyl-2-bromo-phenyl)-acrylic acid methyl ester (8.52 g) in a mixture EtOH/THF (2/1, 150 mL) was added under $N_2$ atmosphere $PtO_2$ (0.45 g). A balloon filled with $H_2$ was set up and $N_2$ was replaced with $H_2$, the reaction was then stirred for 4 h 30 min. The mixture was filtered and the filtrate was evaporated in vacuo. The residue was purified via flash chromatography (hexane/EtOAc, 85/15) affording 3-(4-benzenesulfonyl-2-bromo-phenyl)-propionic acid methyl ester (6.73 g).

Step 4

3-(4-Benzenesulfonyl-2-bromo-phenyl)-propionaldehyde

To a solution of 3-(4-benzenesulfonyl-2-bromo-phenyl)-propionic acid methyl ester (6.73 g, 17.6 mmol) in DCM (100 mL) was added diisobutyl aluminum hydride (1.0M in toluene, 17.6 mL) at −78° C. under Argon. The reaction was maintained at −78° C. for 90 minutes, and MeOH (7 mL ca.) was then added at −78° C. The mixture was allowed to warm to room temperature. HCl (2M) was added and the mixture was extracted twice with DCM. The combined organic extracts were washed with water, dried over $Na_2SO_4$, filtered and evaporated in vacuo. The residue was purified via flash chromatography (hexane/EtOAc, 8/2) affording 3-(4-benzenesulfonyl-2-bromo-phenyl)-propionaldehyde (4.57 g, 74% yield).

Step 5

4-(4-Benzenesulfonyl-2-bromo-phenyl)-1-trimethylsilanyl-butan-2-ol

To a solution of 3-(4-benzenesulfonyl-2-bromo-phenyl)-propionaldehyde (4.77 g, 13.5 mmol) in THF (40 mL) was added trimethylsilylmethylmagnesium chloride (1M in $Et_2O$, 27.3 mL) at −78° C. under Argon atmosphere. The reaction was allowed to reach 0° C. and was stirred for 3 hours, then

---

Step 1

4-Benzenesulfonyl-2-bromo-benzaldehyde

A mixture of 2-bromo-4-fluorobenzaldehyde (10.2 g, 50 mmol) and sodium benzenesulfinate (8.21 g, 50 mmol) in quenched by addition of buffer pH=2 KHSO$_4$/Na$_2$SO$_4$ (10%) at 0° C. The mixture was extracted 3 times with EtOAc and the combined extracts were washed with brine, dried over Na$_2$SO$_4$, filtered and evaporated in vacuo. The residue was purified via flash chromatography (hexane/EtOAc, 8/2) to afford 4-(4-benzenesulfonyl-2-bromo-phenyl)-1-trimethylsilanyl-butan-2-ol (4.60 g, 77% yield).

Step 6

4-Benzenesulfonyl-2-bromo-1-but-3-enyl-benzene

To a solution of 4-(4-benzenesulfonyl-2-bromo-phenyl)-1-trimethylsilanyl-butan-2-ol (4.38 g) in DCM (80 mL) was added BF$_3$.OEt$_2$ (3.76 mL) at 0° C. under N$_2$ atmosphere. The reaction was stirred at 0° C. for 1 h it was then quenched by addition of NaHCO$_3$ (saturated solution). The mixture was extracted twice with DCM and the combined extracts were washed with water, dried over Na$_2$SO$_4$, filtered and concentrated in vacuo. The residue was purified via flash chromatography (hexane/EtOAc, 9/1) to afford 4-benzenesulfonyl-2-bromo-1-but-3-enyl-benzene (3.38 g, 93% yield).

Step 7

(R)-4-(4-Benzenesulfonyl-2-bromo-phenyl)-butane-1,2-diol

A solution of potassium osmate dihydrate (1.19 mg, 0.0034 mmol), hydroquinidine (anthraquinone-1,4-diyl)diether (7.32 mg, 0.00851 mmol), potassium ferricyanide (843 mg, 2.55 mmol) and K$_2$CO$_3$ (357 mg, 2.55 mmol) in t-BuOH/H$_2$O (3.5 mL/4.5 mL) was cooled to 0° C. and a solution of 4-benzenesulfonyl-2-bromo-1-but-3-enyl-benzene (299 mg, 0.851 mmol) in t-BuOH (1 mL) was added. The reaction was maintained at 0° C. for 18 hours, then Na$_2$SO$_3$ (0.68 g) was added at 0° C. The reaction was allowed to warm to room temperature and water was added. The mixture was extracted twice with EtOAc, and the combined extracts were washed with brine, dried over Na$_2$SO$_4$, filtered and concentrated in vacuo. The residue was purified via flash chromatography (hexane/EtOAc) to afford (R)-4-(4-benzenesulfonyl-2-bromo-phenyl)-butane-1,2-diol (193 mg) with 86% ee. Chiral column: Chiralpak AS analytical, hexane/isopropanol (75/25), 1.1 mL/min flow rate.

Step 8

((R)-7-Benzenesulfonyl-chroman-2-yl)-methanol

To a solution of (R)-4-(4-benzenesulfonyl-2-bromo-phenyl)-butane-1,2-diol (1.71 g) in THF (15 mL) were added palladium acetate (30 mg), racemic 2[P(t-Bu)$_2$]-1,1-binaphthyl (53.1 mg) and K$_3$PO$_4$ (1.42 g) under Argon atmosphere. The reaction was heated at reflux for 48 hours; then water was added and the mixture was extracted 3 times with EtOAc. The combined organic extracts were washed with brine, dried over Na$_2$SO$_4$, filtered and concentrated in vacuo. The residue was purified via flash chromatography (hexane/EtOAc, 6/4) to afford ((R)-7-benzenesulfonyl-chroman-2-yl)-methanol (1.20 g).

Step 9

Toluene-4-sulfonic acid (R)-7-benzenesulfonyl-chroman-2-ylmethyl ester

To a solution of ((R)-7-benzenesulfonyl-chroman-2-yl)-methanol (202 mg, 0.663 mol) in DCM (3 mL) were added p-toluensolfonyl chloride (133 mg, 0.696 mmol), triethylamine (0.139 mL, 0.995 mmol) and dimethylaminopyridine (8.1 mg, 0.0663 mmol) at room temperature under Argon atmosphere. The reaction was stirred for 7 hours, then water was added and the mixture was extracted twice with DCM. The combined organic extracts were dried over Na$_2$SO$_4$, filtered and concentrated in vacuo. The residue was purified via flash chromatography (hexane/EtOAc, 7/3) to afford toluene-4-sulfonic acid (R)-7-benzenesulfonyl-chroman-2-ylmethyl ester (278 mg, 91% yield).

Step 10

((R)-7-Benzenesulfonyl-chroman-2-ylmethyl)-methyl-amine

A solution of toluene-4-sulfonic acid (R)-7-benzenesulfonyl-chroman-2-ylmethyl ester (274 mg, 0.6 mmol) and MeNH$_2$ (2M in THF, 5 mL) was heated at 100° C. under microwave conditions for 6 hours. MeNH$_2$ (40% in water, 2 mL) was then added and the mixture was heated at 100° C. under microwave conditions overnight. NaOH (10%) was added and the mixture was extracted 3 times with DCM. The combined organic extracts were washed with water, dried over Na$_2$SO$_4$, filtered and concentrated in vacuo. The residue was purified via flash chromatography to afford the desired product (172 mg). The product was recrystallized from DCM affording 8 mg ((R)-7-benzenesulfonyl-chroman-2-ylmethyl)-methyl-amine with 79% ee and from the evaporation of the mother liquors were recovered an additional 164 mg. Recrystallation from ethanolic HCl yielded the corresponding hydrochloride salt, Mp 271.8-273.0° C.

Similarly, but using sodium 3-fluoro-phenyl sulfinate instead of sodium benzenesulfinate, [(R)-7-(3-Fluoro-benzenesulfonyl)-chroman-2-ylmethyl]-methyl-amine was prepared. MP: 259.0-261.0° C.; MS (M+H)=336.

Example 7

((S)-7-Benzenesulfonyl-chroman-2-ylmethyl)-methyl-amine

The synthetic procedure of Example 7 is outlined in Scheme F below.

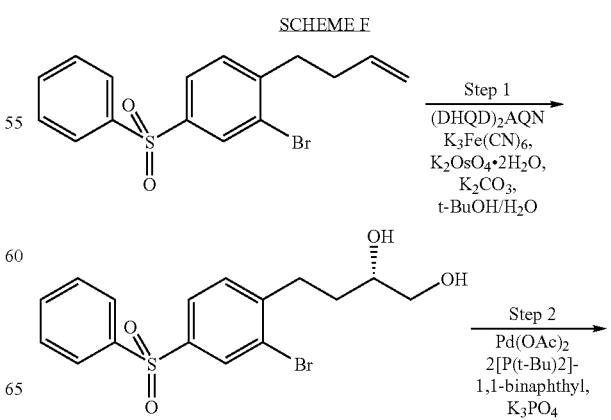

SCHEME F

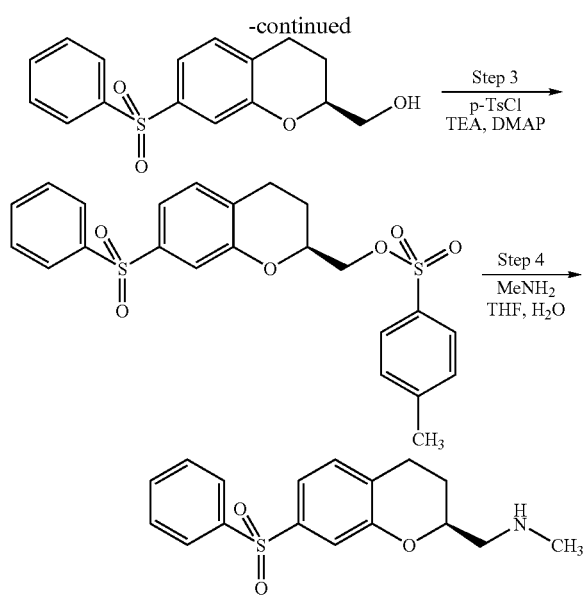

Step 1
(S)-4-(4-Benzenesulfonyl-2-bromo-phenyl)-butane-1,2-diol (S)-4-(4-Benzenesulfonyl-2-bromo-phenyl)-butane-1,2-diol was prepared following the procedure described for the corresponding (R) enantiomer in step 7 of Example 6, but substituting hydroquinine (anthraquinone-1,4-diyl)diether with hydroquinidine (anthraquinone-1,4-diyl)diether.

Step 2
((S)-7-Benzenesulfonyl-chroman-2-yl)-methanol ((S)-7-Benzenesulfonyl-chroman-2-yl)-methanol was prepared following the procedure described for the corresponding (R) enantiomer in step 8 of Example 6, but substituting (S)-4-(4-benzenesulfonyl-2-bromo-phenyl)-butane-1,2-diol for (R)-4-(4-benzenesulfonyl-2-bromo-phenyl)-butane-1,2-diol.

Step 3
Toluene-4-sulfonic acid (S)-7-benzenesulfonyl-chroman-2-ylmethyl ester Toluene-4-sulfonic acid (S)-7-benzenesulfonyl-chroman-2-ylmethyl ester was prepared following the procedure described for the corresponding (R) enantiomer in step 9 of Example 6, but substituting ((S)-7-benzenesulfonyl-chroman-2-yl)-methanol for ((R)-7-benzenesulfonyl-chroman-2-yl)-methanol.

Step 4
((S)-7-Benzenesulfonyl-chroman-2-ylmethyl)-methyl-amine ((S)-7-Benzenesulfonyl-chroman-2-ylmethyl)-methyl-amine was prepared as a hydrochloride salt following the procedure described for the corresponding (R) enantiomer in step 10 of Example 6, but substituting ((S)-7-benzenesulfonyl-chroman-2-ylmethyl)-methyl-amine for ((R)-7-benzenesulfonyl-chroman-2-ylmethyl)-methyl-amine: Mp 270.0-270.4° C.

Example 8

C—[(R)-7-(3-Fluoro-benzenesulfonyl)-chroman-2-yl]-methylamine

The synthetic procedure of Example 8 is outlined in Scheme G below.

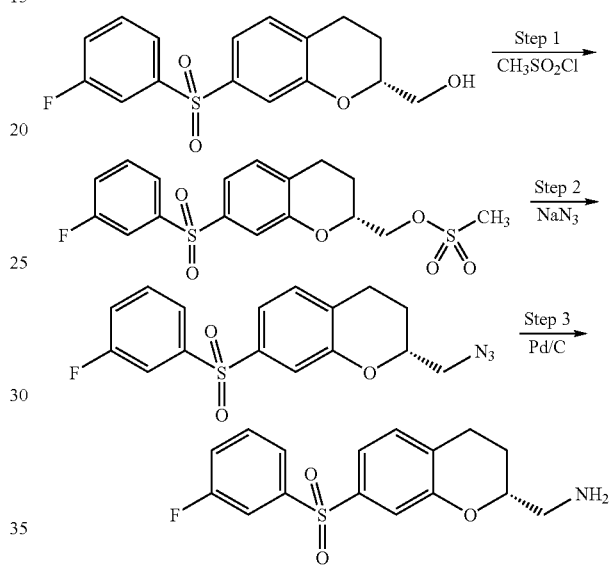

SCHEME G

Step 1 Methanesulfonic acid (R)-7-(3-fluoro-benzenesulfonyl)-chroman-2-ylmethyl ester To a solution of [7-(3-fluoro-benzenesulfonyl)-chroman-2-yl]-methanol (10.0 g, 0.032 mol) in 200 mL of methylene chloride at −10° C. was added methanesulfonyl chloride (2.76 mL, 0.036 mol) and triethylamine (4.95 mL, 0.036 mol). The reaction mixture was stirred for one hour at −10° C. and was then quenched by addition of 10% aqueous $NaHCO_3$. The organic layer was separated, washed with water and brine, dried ($Na_2SO_4$), filtered and concentrated under reduced pressure. The residue was purified by flash chromatography (hexanes:EtOAc 85:15) to give 11.35 g (92%) of methanesulfonic acid (R)-7-(3-fluoro-benzenesulfonyl)-chroman-2-ylmethyl ester.

Step 2 C—[(R)-7-(3-Fluoro-benzenesulfonyl)-chroman-2-yl]-methyl azide

To a solution of methanesulfonic acid (R)-7-(3-fluoro-benzenesulfonyl)-chroman-2-ylmethyl ester (2.0 g, 4.99 mmol) in 30 mL of NMP was added sodium azide (1.55 g, 0.024 mol). The reaction mixture was heated to 75° C. with stirring for two hours. The reaction was quenched by addition of water, and the resulting mixture was extracted with diethyl ether. The combined organic layers were washed with water and brine, dried ($Na_2SO_4$), filtered and concentrated under reduced pressure. The residue was purified by flash chromatography (hexanes:EtOAc 3:2) to give 1.76 g (quantitative) of C—[(R)-7-(3-fluoro-benzenesulfonyl)-chroman-2-yl]-methyl azide.

Step 3 C—[(R)-7-(3-Fluoro-benzenesulfonyl)-chroman-2-yl]-methylamine

To a solution of C—[(R)-7-(3-fluoro-benzenesulfonyl)-chroman-2-yl]-methyl azide (1.76 g, 5.07 mmol) in 30 mL of THF was added 10% Pd/C (0.176 g). The reaction mixture was hydrogenated at 1.5 atmospheric pressure of hydrogen for 18 hours. The mixture was filtered and the filtrated was evaporated under reduced pressure. The residue was purified by flash chromatography (methylene chloride/MeOH 7:3) to give 1.53 g (94%) of C—[(R)-7-(3-Fluoro-benzenesulfonyl)-chroman-2-yl]-methylamine. MP=257.1-258.9° C.; MS (M+H)=322.

Example 9

[(R)-7-(3-Fluoro-benzenesulfonyl)-chroman-2-ylmethyl]-methyl-amine

The synthetic procedure of Example 9 is outlined in Scheme H

SCHEME H

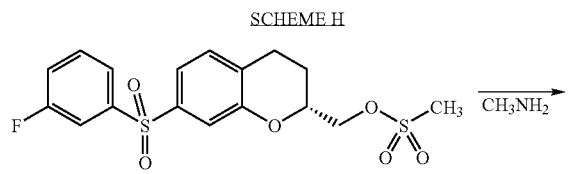

A mixture of methanesulfonic acid (R)-7-(3-fluoro-benzenesulfonyl)-chroman-2-ylmethyl ester (1.145 g, 2.86 mmol) and methylamine hydrate (10.mL) was heated in a sealed tube at 100° C. for 24 hours. The mixture was cooled and extracted with methylene chloride. The combined organic layers were washed with water and brine, dried (Na$_2$SO$_4$), filtered and concentrated under reduced pressure. The residue was purified by flash chromatography (methylene chloride:MeOH 4:1) to give 0.932 g (97%) of [(R)-7-(3-fluoro-benzenesulfonyl)-chroman-2-ylmethyl]-methyl-amine. MP=259.0-261.0° C.; MS (M+H)=336.

Example 10

2-{[(R)-7-(3-Fluoro-benzenesulfonyl)-chroman-2-ylmethyl]-methyl-amino}-acetamide The synthetic procedure of Example 10 is outlined in Scheme I below.

SCHEME I

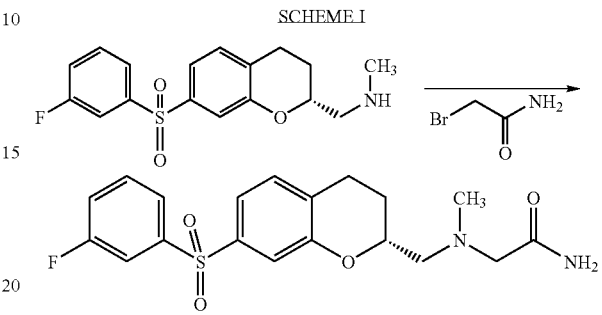

To a solution of [(R)-7-(3-fluoro-benzenesulfonyl)-chroman-2-ylmethyl]-methyl-amine (0.08 g, 0.2.8 mmol) in dry DMF (2 mL) was added triethylamine (0.1 mL, 0.72 mmol) and 3-bromoacetamide (0.32 g, 0.24 mmol). The reaction mixture was stirred for six hours at 60° C., then cooled and quenched by addition of water. The reaction mixture was extracted with diethyl ether, and the combined organic layers were washed with water and brine, dried (MgSO$_4$), filtered and contrated under reduced pressure. Purification of the residue by flash chromatography (MeOH/methylene chloride 1/4) gave 0.08 g of 2-{[(R)-7-(3-fluoro-benzenesulfonyl)-chroman-2-ylmethyl]-methyl-amino}-acetamide as a foam. MS (M+H)=393.

Similarly prepared from (R)-(7-benzenesulfonyl-chroman-2-ylmethyl)-methyl-amine was (R)-2-[(7-Benzenesulfonyl-chroman-2-ylmethyl)-methyl-amino]-acetamide, MS (M+H)=375.

Similarly prepared from (R)—C-(7-benzenesulfonyl-chroman-2-yl)-methylamine was (R)-2-[(7-benzenesulfonyl-chroman-2-ylmethyl)-amino]-acetamide, MS (M+H)=361.

Example 11

2-{[(R)-7-(3-Fluoro-benzenesulfonyl)-chroman-2-ylmethyl]-amino}-N-methyl-acetamide The synthetic procedure of Example 11 is outlined in Scheme J.

SCHEME J

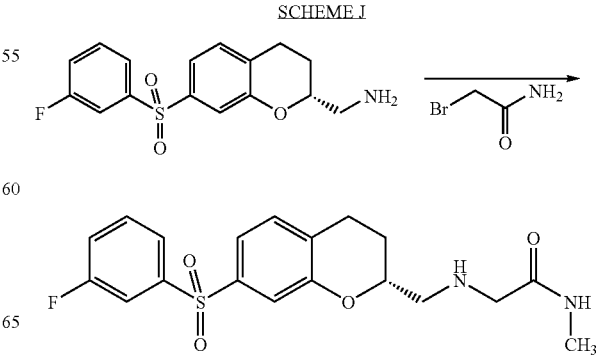

To a solution of C—[(R)-7-(3-Fluoro-benzenesulfonyl)-chroman-2-yl]-methylamine (0.07 g, 0.22 mmol) and 2-chloro-N-methylacetamide (0.023 g, 0.22 mmol) in dry DMF (3 mL) in a sealable tube was added triethylamine (0.1 mL, 0.72 mmol) and NaI (0.01 g). The tube was sealed and heated for four hours at 80° C., then cooled and quenched by addition of water. The reaction mixture was extracted EtOAc, and the combined organic layers were washed with water and brine, dried (Na$_2$SO$_4$), filtered and contrated under reduced pressure. Purification of the residue by flash chromatography (EtOAc:MeOH 99:1 to 97:3) gave 0.044 g of 2-{[(R)-7-(3-fluoro-benzenesulfonyl)-chroman-2-ylmethyl]-amino}-N-methyl-acetamide as a foam. MS (M+H)=393.

Example 12

1-[(R)-7-(3-Fluoro-benzenesulfonyl)-chroman-2-ylmethyl]-3-methyl-urea

The synthetic procedure of Example 1 is outlined in Scheme K.

SCHEME K

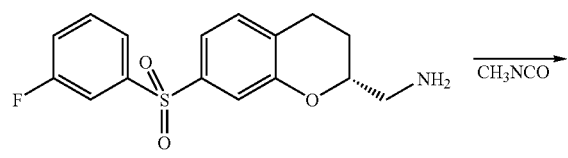

To a solution of C—[(R)-7-(3-Fluoro-benzenesulfonyl)-chroman-2-yl]-methylamine (0.130 g, 0.405 mmol) in methylene chloride (10 mL) at 0° C. was added methyl isocyanate (0.115 g, 2.03 mmol). The mixture was stirred at room temperature for one hour, and was then quenched by addition of MeOH. The mixture was partitioned between water and methylene chloride, and the organic phase was washed with water and brine, dried (Na$_2$SO$_4$), filtered and contrated under reduced pressure. Purification of the residue by flash chromatography (hexanes:EtOAc 1:9) gave 0.153 g of 1-[(R)-7-(3-fluoro-benzenesulfonyl)-chroman-2-ylmethyl]-3-methyl-urea as a foam. MS (M+H)=379.

Similarly prepared from (R)—C-(7-benzenesulfonyl-chroman-2-yl)-methylamine was (R)-1-(7-benzenesulfonyl-chroman-2-ylmethyl)-3-methyl-urea, MS (M+H)=361.

Example 13

N—[(R)-7-(3-Fluoro-benzenesulfonyl)-chroman-2-ylmethyl]-methanesulfonamide

The synthetic procedure of Example 13 is outlined in Scheme L.

SCHEME L

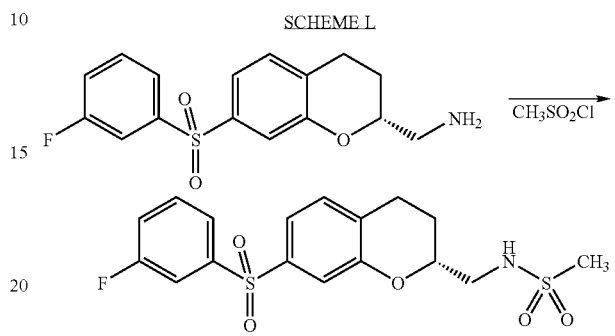

To a solution of C—[(R)-7-(3-Fluoro-benzenesulfonyl)-chroman-2-yl]-methylamine (0.28 g, 0.871 mmol) in methylene chloride (10 mL) was added triethylamine (0.363 mL, 0.26 mmol.) and methanesulfonyl chloride (0.071 g, 0.915 mmol) The mixture was stirred at room temperature for two hours, and was then quenched by addition of water. The mixture was extracted with methylene chloride, and the combined organic layers were washed with water and brine, dried (Na$_2$SO$_4$), filtered and concentrated under reduced pressure. Purification of the residue by flash chromatography (hexanes:EtOAc 1:1) gave 0.296 g of N-[(R)-7-(3-fluoro-benzenesulfonyl)-chroman-2-ylmethyl]-methanesulfonamide as a foam. MS (M+H)=400.

Example 14

(R)-1-(7-Benzenesulfonyl-chroman-2-ylmethyl)-pyrrolidin-3-ol

The synthetic procedure of Example 14 is outlined in Scheme M.

SCHEME M

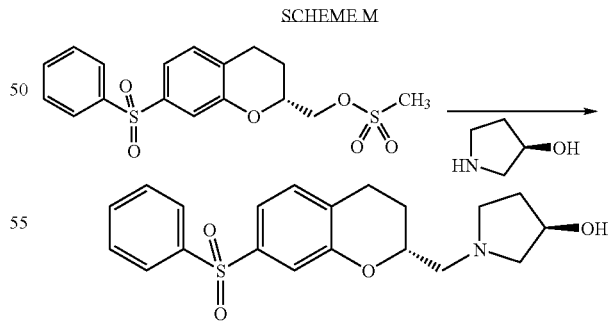

Methanesulfonic acid (R)-7-(3-fluoro-benzenesulfonyl)-chroman-2-ylmethyl ester (0.052 g, 0.13 mmol), (R)-3-hydroxypyrrolidine (0.035 g) and NMP (0.5 mL were sealed in a tube and heated to 110° C. for 18 hours. The reaction mixture was cooled and partitioned between water and diethyl ether. The organic layer was dried over Na$_2$SO$_4$, filtered, and concentrated under reduced pressure. The residue was purified by flash chromatography to give 40.6 mg of (R)-1-(7-benzenesulfonyl-chroman-2-ylmethyl)-pyrrolidin-3-ol, MS (M+H)=374.

Example 15

(R)—N-(7-Benzenesulfonyl-chroman-2-ylmethyl)-2-hydroxy-acetamide

The synthetic procedure of Example 15 is outlined in Scheme N.

SCHEME N

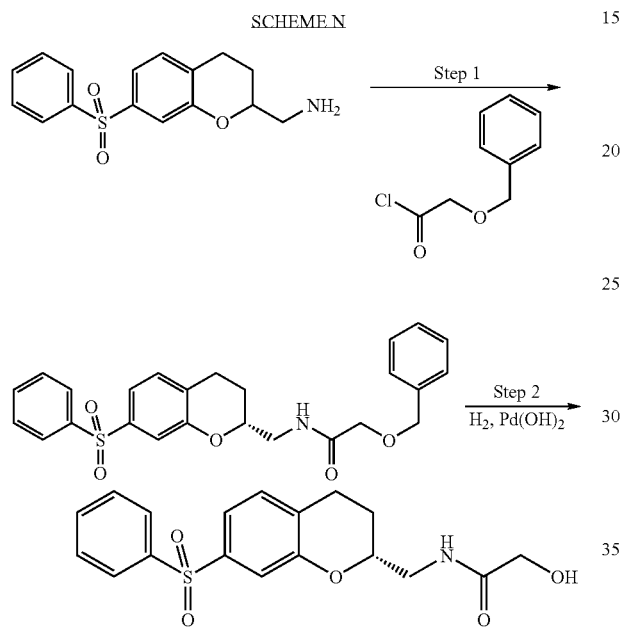

Step 1 N-(7-Benzenesulfonyl-chroman-2-ylmethyl)-2-benzyloxy-acetamide (R)—C-(7-Benzenesulfonyl-chroman-2-yl)-methylamine (130 mg, 0.43 mmol) triethylamine (0.3 mL) and benzyloxy acetyl chloride 77 uL) were added to 3 mL methylene chloride at 0° C. The reaction mixture was stirred at room temperature for three hours and then quenched by addition of water. The mixture was extracted with methylene chloride and the combined organic layers were washed with water and brine, dried (Na$_2$SO$_4$), filtered and contrated under reduced pressure. Purification of the residue by flash chromatography gave 4.34 mg of (R)—N-(7-benzenesulfonyl-chroman-2-yl-methyl)-2-benzyloxy-acetamide.

Step 2 (R)—N-(7-Benzenesulfonyl-chroman-2-ylmethyl)-2-hydroxy-acetamide (R)—N-(7-Benzenesulfonyl-chroman-2-ylmethyl)-2-benzyloxy-acetamide (100 mg, 0.22 mmol) and Perlman's catalyst (12 mg) were added to 15 mL MeOH and hydrogenated for 18 hours at 1.5 atmospheres of hydrogen. The reaction mixture was filtered and the filtrate was concentrated under reduced pressure. The residue was purified by flash chromatography to give 18.7 g of (R)—N-(7-Benzenesulfonyl-chroman-2-ylmethyl)-2-hydroxy-acetamide, MS (M+H)= 362.

Example 16

(R)-2-[(7-Benzenesulfonyl-chroman-2-ylmethyl)-methyl-amino]-ethanol

The synthetic procedure of Example 16 is outlined in Scheme O.

SCHEME O

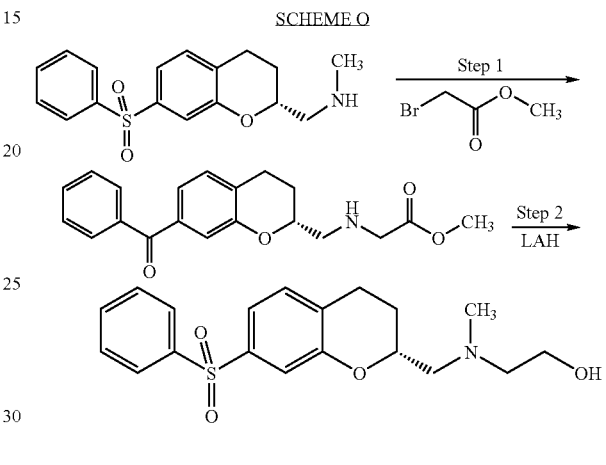

Step 1 (R)-[(7-Benzenesulfonyl-chroman-2-ylmethyl)-amino]-acetic acid methyl ester (R)-(7-Benzenesulfonyl-chroman-2-ylmethyl)-methyl-amine (81 mg, 2.6 mmol) and triethylamine (0.2 mL) were added to 0.5 mL NMP and the mixture was cooled to 0° C. with stirring. Methyl 2-bromoacetate (26 uL) was added, and the reaction mixture was stirred for two hours at room temperature, then quenched by addition of water. The mixture was extracted with methylene chloride and the combined organic layers were washed with water and brine, dried (Na$_2$SO$_4$), filtered and contrated under reduced pressure. Purification of the residue by flash chromatography gave 40 mg of (R)-[(7-benzenesulfonyl-chroman-2-ylmethyl)-amino]-acetic acid methyl ester.

Step 2 (R)-2-[(7-Benzenesulfonyl-chroman-2-ylmethyl)-methyl-amino]-ethanol (R)-[(7-benzenesulfonyl-chroman-2-ylmethyl)-amino]-acetic acid methyl ester (40 mg, 1 mmol) was dissolved in 2 mL dry THF under Ar atmosphere. LAH (0.25 mL of 1M solution in THF) was added dropwise, and the reaction mixture was stirred for one hour. The reaction was quenched by addition of aqueous sodium sulfate solution. The mixture was extracted with methylene chloride and the combined organic layers were washed with water and brine, dried (Na$_2$SO$_4$), filtered and contrated under reduced pressure. The residue was recrystallized from diethyl ether and 1 M HCl in EtOH to give 32.2 mg of (R)-2-[(7-Benzenesulfonyl-chroman-2-ylmethyl)-methyl-amino]-ethanol as a hydrochloride, MS (M+H)=362.

Example 17

(R)—N-(7-Benzenesulfonyl-chroman-2-ylmethyl)-2-(R)-hydroxy-propionamide

The synthetic procedure of Example 16 is outlined in Scheme P.

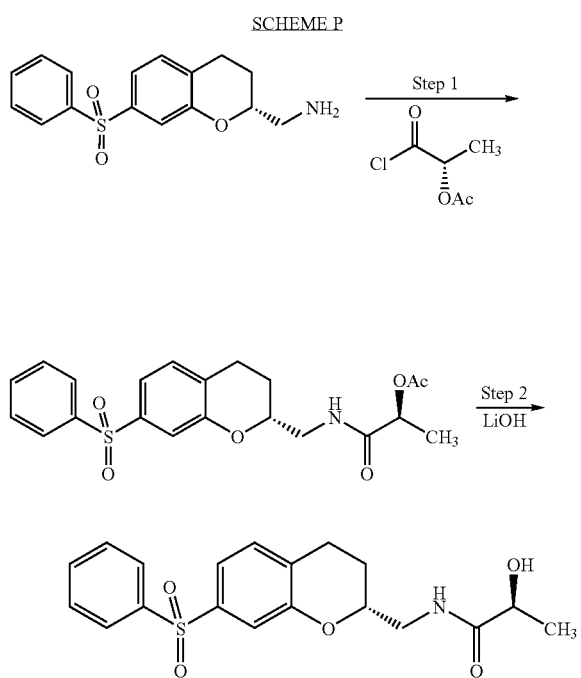

Step 1 (R)-Acetic acid 1-[(7-benzenesulfonyl-chroman-2-ylmethyl)-carbamoyl]-ethyl ester (R)—C-(7-Benzenesulfonyl-chroman-2-yl)-methylamine (57 mg, 0.19 mmol) triethylamine (0.02 mL) and acetic acid 1-(R)-chlorocarbonyl-ethyl ester were added to 1 mL methylene chloride, and the mixture was stirred for two hours at room temperature. The reaction was quenched by addition of water, and the mixture was extracted with methylene chloride. The combined organic layers were washed with water and brine, dried ($Na_2SO_4$), filtered and contrated under reduced pressure. Purification of the residue by flash chromatography gave 7.59 mg of (R)-acetic acid 1-[(7-benzenesulfonyl-chroman-2-ylmethyl)-carbamoyl]-ethyl ester.

Step 2 (R)—N-(7-Benzenesulfonyl-chroman-2-ylmethyl)-2-(R)-hydroxy-propionamide (R)-Acetic acid 1-[(7-benzenesulfonyl-chroman-2-ylmethyl)-carbamoyl]-ethyl ester (7.59 mg) was dissolved in 1 mL MeOH, and water (0.25 mL) and LiOH (200 mg) were added. The reaction was stirred at room temperature for two hours, then quenched by addition of water. Crystals formed and were collected by filtration, washed with water and dried under vacuum to give 37 mg of (R)—N-(7-Benzenesulfonyl-chroman-2-ylmethyl)-2-(R)-hydroxy-propionamide. MP=129.5-131.5° C.; MS (M–H)=374.

Example 18

(R)-(7-Benzenesulfonyl-chroman-2-ylmethyl)-((R)-1-phenyl-ethyl)-amine

The synthetic procedure of Example 18 is outlined in Scheme Q.

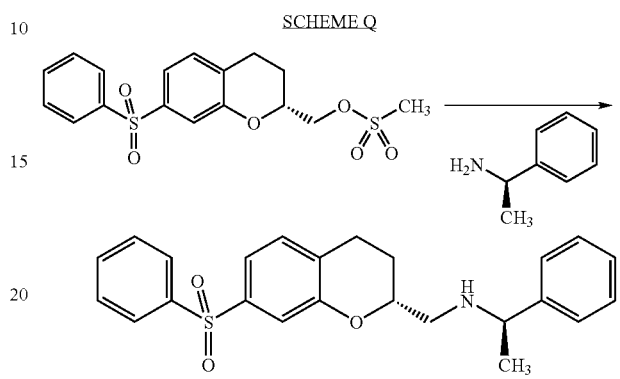

Methanesulfonic acid (R)-7-(3-fluoro-benzenesulfonyl)-chroman-2-ylmethyl ester (1.43 g, 3.7 mmol) and (R)-1-phenyl ethylamine (3 mL) were added to NMP (5 mL), and the reaction mixture was stirred for 18 hours at 110° C. The reaction mixture was cooled to room temperature, quenched by addition of water, and made basic to pH 14 by addition of 1M aqueous NaOH. The mixture was extracted with diethyl ether, and the combined organic layers were washed with brine, dried over $Na_2SO_4$, filtered, and concentrated under reduced pressure. The residue was purified by flash chromatography (0-30% EtOAc/hexanes) to give 1.2 g of (R)-(7-benzenesulfonyl-chroman-2-ylmethyl)-((R)-1-phenyl-ethyl)-aminel, MS (M+H)=408.

Example 19

(R)-(7-Benzenesulfonyl-chroman-2-ylmethyl)-urea

The synthetic procedure of Example 19 is outlined in Scheme R.

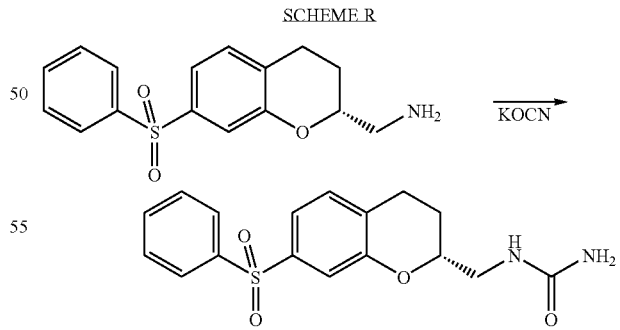

C—(R)-(7-Benzenesulfonyl-chroman-2-yl)-methylamine (0.047 g, 0.15 mmol) was added to a mixture of 1 mL EtOH, 0.1 mL HOAc and 0.2 mL water. The mixture was cooled in an ice bath, and 0.2 mL of 20% aqueous KOCN was added. The reaction mixture was stirred for two hours at room temperature, then extracted with EtOAc. The combined organic layers were washed with water, evaporated under reduced pressure, and the residue was taken up in MeOH/methylene chloride (1:1), dried ($Na_2SO_4$), filtered and concentrated under reduced pressure to give 0.03 g of (R)-(7-Benzenesulfonyl-chroman-2-ylmethyl)-urea, MS (M+H)=347.

Example 20

(R)-[(7-Benzenesulfonyl-chroman-2-ylmethyl)-amino]-acetonitrile

The synthetic procedure of Example 20 is outlined in Scheme S.

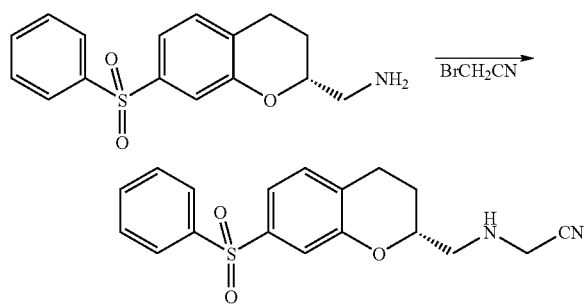

SCHEME S

C—(R)-(7-Benzenesulfonyl-chroman-2-yl)-methylamine (0.053 g, 0.175 mmol) and triethylamine (0.2 mL) were added to 2 mL methylene chloride, and the mixture was cooled to 0° C. Bromoacetamide (12 mL) was added dropwise to the cold stirring solution, and stirring was continued at room temperature for 18 hours. The reaction was quenched by addition of water and extracted with methylene chloride. The combined organic layers were dried ($Na_2SO_4$), filtered and concentrated under reduced pressure. The residue was purified by flash chromatography (MeOH/methylene chloride 0:1 to 2.5:1) to give 0.034 g of (R)-[(7-benzenesulfonyl-chroman-2-ylmethyl)-amino]-acetonitrile, MS (M+H)=343.

Example 21

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
| --- | --- |
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 microliters of formulation per actuation. A typical dosing schedule is 2-4 sprays every 4-12 hours.

Example 22

Radioligand Binding Studies

This example illustrates in vitro radioligand binding studies of compound of formula I.

The binding activity of compounds of this invention in vitro was determined as follows. Duplicate determinations of 5-$HT_6$ ligand affinity were made by competing for binding of [$^3$H]LSD in cell membranes derived from HEK293 cells stably expressing recombinant human 5-$HT_6$ receptor. Duplicate determinations of 5-$HT_{2A}$ ligand affinity were made by competing for binding of [$^3$H]Ketanserin (3-(2-(4-(4-fluorobenzoyl)piperidinol)ethyl)-2,4(1H,3H)-quinazolinedione) in cell membranes derived from CHO-K1 cells stably expressing recombinant human 5-$HT_{2A}$ receptor. Membranes were prepared from HEK 293 cell lines by the method described by Monsma et al., Molecular Pharmacology, Vol. 43 pp. 320-327 (1993), and from CHO-K1 cell lines as described by Bonhaus et al., Br J Pharmacol. June; 115(4): 622-8 (1995).

For estimation of affinity at the 5-$HT_6$ receptor, all determinations were made in assay buffer containing 50 mM Tris-HCl, 10 mM $MgSO_4$, 0.5 mM EDTA, 1 mM ascorbic acid, pH 7.4 at 37° C., in a 250 microliter reaction volume. For estimation of affinity at the 5-$HT_{2A}$ receptor all determinations were made in assay buffer containing 50 mM Tris-HCl, 5 mM ascorbic acid, 4 mM CaCl2, pH 7.4 at 32° C., in a 250 microliter reaction volume.

Assay tubes containing [$^3$H] LSD or [$^3$H]Ketanserin (5 nM), competing ligand, and membrane were incubated in a shaking water bath for 75 min. at 37° C. (for 5-$HT_6$) or 60 min. at 32° C. (for 5-$HT_{2A}$), filtered onto Packard GF-B plates (pre-soaked with 0.3% PEI) using a Packard 96 well cell harvester and washed 3 times in ice cold 50 mM Tris-HCl. Bound [$^3$H] LSD or [$^3$H]Ketanserin were determined as radioactive counts per minute using Packard TopCount.

Displacement of [$^3$H]LSD or [$^3$H]Ketanserin from the binding sites was quantified by fitting concentration-binding data to a 4-parameter logistic equation:

$$\text{binding} = \text{basal} + \left( \frac{\text{Bmax} - \text{basal}}{1 + 10^{-Hill(\log[ligand] - \log IC_{50})}} \right)$$

where Hill is the Hill slope, [ligand] is the concentration of competing radioligand and $IC_{50}$ is the concentration of radioligand producing half-maximal specific binding of radioligand. The specific binding window is the difference between the Bmax and the basal parameters. Using the procedures of this Example, compounds of Formula I were tested and found to be selective 5-$HT_6$ antagonists, selective 5-$HT_{2A}$ antagonists, or both. For example, the compound (S)-(7-benzenesulfonyl-chroman-2-ylmethyl)-methyl-amine exhibited a pKi of approximately 10.0 for the 5-HT6 receptor, and a pKi of approximately 7.25 for the 5-HT2A receptor.

Example 23

Cognition Enhancement

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47-59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of formula I:

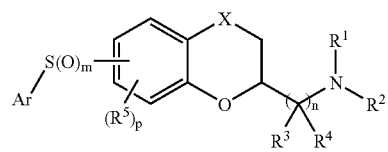

or a pharmaceutically acceptable salt thereof, wherein:
m is from 0 to 2:
n is from 1 to 3;
p is from 0 to 3;
Ar is optionally substituted aryl or optionally substituted heteroaryl;
X is —C(O)— or —CR$^a$R$^b$—,
wherein:
R$^a$ is hydrogen or C$_{1-6}$alkyl; and
R$^b$ is hydrogen, C$_{1-6}$alkyl or hydroxy;
R$^1$ and R$^2$ each independently is:
hydrogen;
C$_{1-6}$alkyl;
hydroxy-C$_{1-6}$ alkyl; or
—CH$_2$—C(O)—OCH$_3$;
or one of R$^1$ and R$^2$ is hydrogen or C$_{1-6}$ alkyl and the other is:
a five- or six-membered heteroaryl or heterocyclyl that contains one or two nitrogens and which is optionally substituted with hydroxyl;
C$_{3-8}$ cycloalkyl;
aryl-C$_{1-6}$ alkyl; or
—(CH$_2$)$_r$—Y—R$^h$,
wherein:
Y is —C(O)— or —SO$_2$—;
r is 0, 1 or 2; and
R$^h$ is:
C$_{1-6}$alkyl;
C$_{3-8}$ cycloalkyl;
C$_{1-6}$alkoxy;
cyano-C$_{1-6}$alkyl;
halo-C$_{1-6}$alkyl;
hydroxy;
amino;
N—C$_{1-6}$alkylamino;
N,N-di-C$_{1-6}$alkylamino;
hydroxy-C$_{1-6}$alkyl wherein the hydroxy group may be acetylated;
aryl;
aryl-C$_{1-6}$alkyl; or
aryl-C$_{1-6}$alkyloxy-C$_{1-6}$alkyl;
or R$^1$ and R$^2$ together with the nitrogen to which they are attached may form a three- to seven-membered ring that optionally contains an additional heteroatom selected from N, O and S and which is optionally substituted with hydroxyl;
or R$^1$ and R$^2$ together with the nitrogen to which they are attached may form a guanidinyl group or an amidinyl group;
R$^3$ and R$^4$ each independently is hydrogen or C$_{1-6}$ alkyl;
or one of R$^3$ and R$^4$ together with one of R$^1$ and R$^2$ and the atoms to which they are attached may form a five or six-membered ring;
or R$^3$ and R$^4$ together may form =NR$^c$ wherein R$^c$ is hydrogen or C$_{1-6}$ alkyl; and
each R$^5$ is independently halo, C$_{1-6}$ alkyl, halo-C$_{1-6}$ alkyl, hetero-C$_{1-6}$ alkyl, cyano, —SO$_2$R$^d$, —C(=O)—NR$^e$R$^f$, —SR$^d$, —C(=O)—R$^g$, where each of R$^d$, R$^e$ and R$^f$ is independently hydrogen or C$_{1-6}$ alkyl and R$^g$ is hydrogen, C$_{1-6}$ alkyl, hydroxy or C$_{1-6}$ alkoxy.

2. The compound of claim 1, wherein n is 1.
3. The compound of claim 2, wherein R$^3$ and R$^4$ are hydrogen.
4. The compound of claim 3, wherein R$^1$ and R$^2$ each independently is hydrogen or C$_{1-6}$alkyl.

5. The compound of claim 3, wherein Ar is optionally substituted phenyl.
6. The compound of claim 5, wherein p is 0 or 1.
7. The compound of claim 6, wherein X is —CR$^a$R$^b$—.
8. The compound of claim 7, wherein R$^a$ and R$^b$ are hydrogen.
9. The compound of claim 8, wherein R$^1$ is hydrogen or C$_{1-6}$alkyl, and R$^2$ is —(CH$_2$)$_r$—Y—R$^h$.
10. The compound of claim 1, wherein said compound is of formula II:

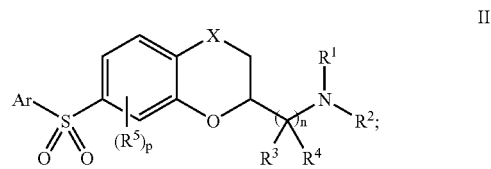

and wherein n, p, X, Ar, R$^1$, R$^2$, R$^3$, R$^4$ and R$^5$ are as recited in claim 1.

11. The compound of claim 10, wherein n is 1.
12. The compound of claim 11, wherein R$^3$ and R$^4$ are hydrogen.
13. The compound of claim 12, wherein p is 0 or 1.
14. The compound of claim 12, wherein R$^1$ and R$^2$ each independently is hydrogen or C$_{1-6}$ alkyl.
15. The compound of claim 12, wherein Ar is optionally substituted phenyl.
16. The compound of claim 15, wherein X is —CR$^a$R$^b$—.
17. The compound of claim 16, wherein R$^a$ and R$^b$ are hydrogen.
18. The compound of claim 17, wherein R$^1$ is hydrogen or C$_{1-6}$alkyl, and R$^2$ is —(CH$_2$)$_r$—Y—R$^h$.
19. The compound of claim 10, wherein said compound is of the formula III:

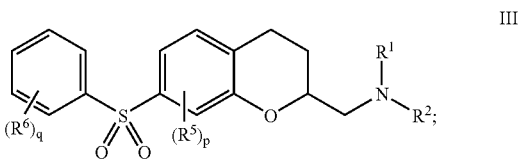

wherein:
q is from 0 to 4;
each R$^6$ is independently halo, C$_{1-6}$ alkyl, halo-C$_{1-6}$ alkyl, hetero-C$_{1-6}$ alkyl, cyano, —SO$_2$R$^d$, —C(=O)—NR$^e$R$^f$, —SR$^d$, —C(=O)—R$^g$, where each of R$^d$, R$^e$ and R$^f$ is independently hydrogen or C$_{1-6}$ alkyl and R$^g$ is hydrogen, C$_{1-6}$ alkyl, hydroxy or C$_{1-6}$alkoxy; and
p, R$^1$, R$^2$ and R$^5$ are as recited in claim 10.

20. The compound of claim 19, wherein q is 0 or 1 and R$^6$ is halo.
21. The compound of claim 19, wherein R$^1$ is hydrogen and R$^2$ is methyl.
22. The compound of claim 19, wherein R$^1$ is hydrogen or C$_{1-6}$alkyl, and R$^2$ is —(CH$_2$)$_r$—Y—R$^h$.

23. The compound of claim 19, wherein said compound is of the formula IV:

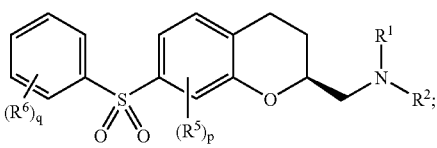

wherein p, q, $R^1$, $R^2$, $R^5$ and $R^6$ are as recited in claim 19.

24. The compound of claim 19, wherein said compound is of the formula V:

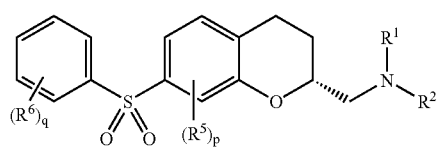

wherein p, q, $R^1$, $R^2$, $R^5$ and $R^6$ are as recited in claim 19.

25. A pharmaceutical composition comprising an effective amount of the compound of claim 1 in admixture with a pharmaceutically acceptable carrier.

26. A method for treating a central nervous system disease selected from selected from psychoses, schizophrenia, manic depressions, neurological disorders, memory disorders, attention deficit disorder, Parkinson's disease, amyotrophic lateral sclerosis, Alzheimer's disease, food uptake disorders, and Huntington's disease, said method comprising administering to a subject in need thereof a therapeutically effective amount of a compound of claim 1.

27. The compound of claim 1, wherein said compound is selected from the group consisting of:
7-Benzenesulfonyl-2-methylaminomethyl-chroman-4-one;
7-Benzenesulfonyl-2-methylaminomethyl-chroman-4-ol;
(7-Benzenesulfonyl-chroman-2-ylmethyl)-methyl-amine;
7-Benzenesulfonyl-4-methyl-2-methylaminomethyl-chroman-4-ol;
7-Benzenesulfonyl-2-methylaminomethyl-chroman-8-carboxylic acid methylamide;
(R)-(7-Benzenesulfonyl-chroman-2-ylmethyl)-methyl-amine;
(S)-(7-Benzenesulfonyl-chroman-2-ylmethyl)-methyl-amine;
(R)-2-[(7-Benzenesulfonyl-chroman-2-ylmethyl)-amino]-acetamide;
(R)—C-(7-Benzenesulfonyl-chroman-2-yl)-methyl-amine;
(R)-[(7-Benzenesulfonyl-chroman-2-ylmethyl)-methoxycarbonylmethyl-amino]-acetic acid methyl ester;
(R)-2-[(7-Benzenesulfonyl-chroman-2-ylmethyl)-(2-hydroxy-ethyl)-amino]ethanol;
2-[(7-Benzenesulfonyl-chroman-2-ylmethyl)-amino]ethanol;
(R)-2-[(7-Benzenesulfonyl-chroman-2-ylmethyl)-methyl-amino]-acetamide;
(R)-1-(7-Benzenesulfonyl-chroman-2-ylmethyl)-pyrrolidin-(R)-3-ol;
(R)-1-(7-Benzenesulfonyl-chroman-2-ylmethyl)-pyrrolidin-(S)-3-ol;
(R)—N-(7-Benzenesulfonyl-chroman-2-ylmethyl)-N-methyl-methanesulfonamide;
(R)—N-(7-Benzenesulfonyl-chroman-2-ylmethyl)-N-methyl-acetamide;
(R)—N-(7-Benzenesulfonyl-chroman-2-ylmethyl)-methanesulfonamide;
(R)—N-(7-Benzenesulfonyl-chroman-2-ylmethyl)-acetamide;
(R)—N-(7-Benzenesulfonyl-chroman-2-ylmethyl)-2-benzyloxy-acetamide;
(R)-1-(7-Benzenesulfonyl-chroman-2-ylmethyl)-1,3-dimethyl-urea;
(R)-(7-Benzenesulfonyl-chroman-2-ylmethyl)-urea;
(R)-(7-Benzenesulfonyl-chroman-2-ylmethyl)-methyl-carbamic acid methyl ester;
(R)-1-(7-Benzenesulfonyl-chroman-2-ylmethyl)-1-methyl-urea;
(R)—N-(7-Benzenesulfonyl-chroman-2-ylmethyl)-2-hydroxy-acetamide;
(R)—N-(7-Benzenesulfonyl-chroman-2-ylmethyl)-isobutyramide;
(R)-Ethanesulfonic acid (7-benzenesulfonyl-chroman-2-ylmethyl)-amide;
(R)-1-(7-Benzenesulfonyl-chroman-2-ylmethyl)-3-methyl-urea;
(R)-Acetic acid 1-[(7-benzenesulfonyl-chroman-2-ylmethyl)-carbamoyl]-ethyl ester;
(R)—N-(7-Benzenesulfonyl-chroman-2-ylmethyl)-2-hydroxy-propionamide;
(R)-1-[(7-Benzenesulfonyl-chroman-2-ylmethyl)-amino]-propan-2-ol;
(R)-2-[(7-Benzenesulfonyl-chroman-2-ylmethyl)-methyl-amino]-ethanol;
(R)-2-[(7-Benzenesulfonyl-chroman-2-ylmethyl)-amino]-N-methyl-acetamide;
(R)-2-[(7-Benzenesulfonyl-chroman-2-ylmethyl)-methylcarbamoylmethyl-amino]-N-methyl-acetamide;
(R)-[7-(3-Fluoro-benzenesulfonyl)-chroman-2-ylmethyl]-methyl-amine;
(R)-Cyclopropanesulfonic acid (7-benzenesulfonyl-chroman-2-ylmethyl)-methyl-amide;
(R)-Cyclopropanesulfonic acid (7-benzenesulfonyl-chroman-2-ylmethyl)-amide;
(R)-[(7-Benzenesulfonyl-chroman-2-ylmethyl)-methyl-amino]-acetonitrile;
(R)-Propane-1-sulfonic acid (7-benzenesulfonyl-chroman-2-ylmethyl)-amide;
(R)-2,2,2-Trifluoro-ethanesulfonic acid (7-benzenesulfonyl-chroman-2-ylmethyl)-amide;
(R)-Propane-2-sulfonic acid (7-benzenesulfonyl-chroman-2-ylmethyl)-amide;
(R)-2-{[7-(3-Fluoro-benzenesulfonyl)-chroman-2-ylmethyl]-amino}-acetamide;
(R)-Propane-1-sulfonic acid (7-benzenesulfonyl-chroman-2-ylmethyl)-methyl-amide;
(R)-2-{[7-(3-Fluoro-benzenesulfonyl)-chroman-2-ylmethyl]-amino}-ethanol;
(R)-Ethanesulfonic acid (7-benzenesulfonyl-chroman-2-ylmethyl)-methyl-amide;
(R)—C-[7-(3-Fluoro-benzenesulfonyl)-chroman-2-yl]-methylamine;
(R)-1-(7-Benzenesulfonyl-chroman-2-ylmethyl)-piperidin-4-ol;
(R)—N-(7-Benzenesulfonyl-chroman-2-ylmethyl)-C,C,C-trifluoro-methanesulfonamide;
(R)—N-(7-Benzenesulfonyl-chroman-2-ylmethyl)-benzenesulfonamide;

(R)-N-[7-(3-Fluoro-benzenesulfonyl)-chroman-2-ylmethyl]-methanesulfonamide;
(R)-Ethanesulfonic acid [7-(3-fluoro-benzenesulfonyl)-chroman-2-ylmethyl]-amide;
(R)-Cycloproanesulfonic acid [7-(3-fluoro-benzenesulfonyl)-chroman-2-ylmethyl]-amide;
(R)-Propane-2-sulfonic acid [7-(3-fluoro-benzenesulfonyl)-chroman-2-ylmethyl]-amide;
(R)-[7-(3-Fluoro-benzenesulfonyl)-chroman-2-ylmethyl]-urea;
(R)-[7-(3-Fluoro-benzenesulfonyl)-chroman-2-ylmethy]-3-methyl-urea;
(R)-2-{[7-(3-Fluoro-benzenesulfonyl)-chroman-2-ylmethyl]-amino}-N-methyl-acetamide;
(R)—N-[7-(3-Fluoro-benzenesulfonyl)-chroman-2-ylmethyl]-N-methyl-methanesulfonamide;
(R)-1-[7-(3-Fluoro-benzenesulfonyl)-chroman-2-ylmethyl]-1-methyl-urea;
(R)-1-[7-(3-Fluoro-benzenesulfonyl)-chroman-2-ylmethyl]-1,3-dimethyl-urea;
(R)-Ethanesulfonic acid [7-(3-fluoro-benzenesulfonyl)-chroman-2-ylmethyl]-methyl-amide;
(R)-2-{[7-(3-Fluoro-benzenesulfonyl)-chroman-2-ylmethyl]-methyl-amino}acetamide;
(R)-[7-(3-Fluoro-benzenesulfonyl)-chroman-2-ylmethyl]-carbamic acid ethyl ester;
(R)-[7-(3-Fluoro-benzenesulfonyl)-chroman-2-ylmethyl]-(1-(R)-phenyl-ethyl)-amine;
(R)-1-[7-(3-Fluoro-benzenesulfonyl)-chroman-2-ylmethyl]-3-methyl-urea;
(R)-(7-Benzenesulfonyl-chroman-2-ylmethyl)-(1-phenyl-ethyl)-amine;
(R)-1-[(7-Benzene sulfonyl-chroman-2-ylmethyl)-amino]-(S)-propan-2-ol;
(R)-2-[(7-Benzenesulfonyl-chroman-2-ylmethyl)-amino]-(R)-propan-1-ol;
(R)-2-[(7-Benzenesulfonyl-chroman-2-ylmethyl)-amino]-(S)-propan-1-ol;
(R)-2-[(7-Benzenesulfonyl-chroman-2-ylmethyl)-amino]-propane-1,3-diol; and
(R)-3-[(7-Benzenesulfonyl-chroman-2-ylmethyl)-amino]-(R)-propane-1,2-diol.

* * * * *